(12) United States Patent
Fang et al.

(10) Patent No.: US 12,349,944 B2
(45) Date of Patent: *Jul. 8, 2025

(54) IMPLANT SYSTEM AND METHOD FOR JOINT FUSION

(71) Applicant: Orthofix US LLC, Lewisville, TX (US)

(72) Inventors: Samuel Fang, Plano, TX (US); Kevin G. Roberts, Frisco, TX (US)

(73) Assignee: Orthofix US LLC, Lewisville, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/505,320

(22) Filed: Nov. 9, 2023

(65) Prior Publication Data

US 2024/0074796 A1    Mar. 7, 2024

Related U.S. Application Data

(63) Continuation of application No. 17/190,280, filed on Mar. 2, 2021, now Pat. No. 11,918,257.

(Continued)

(51) Int. Cl.
*A61B 17/86* (2006.01)
*A61B 17/70* (2006.01)
*B33Y 80/00* (2015.01)

(52) U.S. Cl.
CPC ........ *A61B 17/7055* (2013.01); *A61B 17/863* (2013.01); *A61B 17/864* (2013.01); *A61B 17/866* (2013.01); *B33Y 80/00* (2014.12)

(58) Field of Classification Search
CPC ... A61B 17/86; A61B 17/8625; A61B 17/863; A61B 17/864; A61B 17/866;

(Continued)

(56) References Cited

U.S. PATENT DOCUMENTS

| 5,360,448 A | 1/1994 | Thramann |
|---|---|---|
| 5,536,127 A | 7/1996 | Pennig |

(Continued)

FOREIGN PATENT DOCUMENTS

| MU | 910210-4 U2 | 7/2013 |
|---|---|---|
| WO | 2019152737 A1 | 8/2019 |

OTHER PUBLICATIONS

European Patent Office, Supplementary European Search Report, European Patent Application No. 21764231.3, dated Jul. 9, 2024, 12 pages.

(Continued)

*Primary Examiner* — Eduardo C Robert
*Assistant Examiner* — Christina Negrelli-Rodriguez
(74) *Attorney, Agent, or Firm* — Haynes and Boone, LLP

(57) ABSTRACT

Implant systems and methods treatment of a joint include a distal portion, a middle portion, and a proximal portion. The distal portion may include a thread having a first thread minor, a first thread major, and a first pitch. The distal portion also may have a reverse cut, helical fenestration formed through the thread. The middle portion may be devoid of threads and may include a porous outer surface structure to promote bony integration, the porous outer surface structure having a leading end and a trailing end, with the leading end having a diameter larger than the first thread minor. The proximal portion may include a proximal thread having a second thread minor, a second thread major, and a second pitch. The second thread minor may be substantially the same width as the trailing end of the middle portion.

20 Claims, 16 Drawing Sheets

Related U.S. Application Data

(60) Provisional application No. 62/985,036, filed on Mar. 4, 2020.

(58) Field of Classification Search
CPC ... A61B 17/7074; A61B 17/68; A61B 17/686; A61B 2017/681; A61F 2/46
USPC .......................................... 606/300–321, 96
See application file for complete search history.

(56) References Cited

U.S. PATENT DOCUMENTS

| | | | |
|---|---|---|---|
| 5,772,661 | A * | 6/1998 | Michelson ............ A61B 17/025 606/279 |
| 6,053,916 | A | 4/2000 | Moore |
| 6,319,254 | B1 | 11/2001 | Giet et al. |
| 6,565,573 | B1 | 5/2003 | Ferrante et al. |
| 6,635,059 | B2 | 10/2003 | Randall et al. |
| 7,708,766 | B2 | 5/2010 | Anderson et al. |
| 8,394,132 | B2 | 3/2013 | Lewis et al. |
| 8,900,279 | B2 | 12/2014 | Assell et al. |
| 9,271,742 | B2 | 3/2016 | Asfora |
| 9,271,743 | B2 | 3/2016 | Asfora |
| 9,295,488 | B2 | 3/2016 | Asfora |
| 9,358,057 | B1 | 6/2016 | Whipple et al. |
| 9,526,548 | B2 | 12/2016 | Asfora |
| 9,566,100 | B2 | 2/2017 | Asfora |
| 9,668,781 | B2 | 6/2017 | Stark |
| 9,943,340 | B2 | 4/2018 | Whipple et al. |
| 10,052,140 | B2 * | 8/2018 | Krause ............... A61B 17/7037 |
| 10,058,368 | B2 | 8/2018 | Orbay et al. |
| 10,123,825 | B2 | 11/2018 | Whipple et al. |
| 10,179,014 | B1 | 1/2019 | Menmuir et al. |
| 10,179,015 | B2 | 1/2019 | Lavigne et al. |
| 10,251,688 | B2 | 4/2019 | Asfora |
| 10,307,194 | B2 | 6/2019 | Tempco |
| 10,363,076 | B2 | 7/2019 | Werner |
| 10,420,597 | B2 | 9/2019 | Papangelou et al. |
| 10,426,533 | B2 | 10/2019 | Mauldin et al. |
| 11,918,257 | B2 * | 3/2024 | Fang .................. A61B 17/8645 |
| 2003/0187447 | A1 | 10/2003 | Ferrante |
| 2005/0038438 | A1 | 2/2005 | Anderson et al. |
| 2005/0149191 | A1 | 7/2005 | Cragg et al. |
| 2009/0024174 | A1 | 1/2009 | Stark |
| 2010/0106200 | A1 | 4/2010 | Stark |
| 2011/0276095 | A1 | 11/2011 | Bar et al. |
| 2013/0238036 | A1 | 9/2013 | Sinha |
| 2013/0245763 | A1 | 9/2013 | Mauldin |
| 2014/0012340 | A1 | 1/2014 | Beck et al. |
| 2014/0039565 | A1 | 2/2014 | Martineau et al. |
| 2016/0143742 | A1 | 5/2016 | Asfora |
| 2016/0157897 | A1 | 6/2016 | Vaidya |
| 2016/0157908 | A1 | 6/2016 | Cawley et al. |
| 2016/0287301 | A1 | 10/2016 | Mehl et al. |
| 2016/0310188 | A1 | 10/2016 | Marino et al. |
| 2017/0224393 | A1 | 8/2017 | Lavigne et al. |
| 2017/0238973 | A1 | 8/2017 | Stark |
| 2017/0246000 | A1 | 8/2017 | Pavlov et al. |
| 2018/0092677 | A1 | 4/2018 | Peterson et al. |
| 2018/0199970 | A1 | 7/2018 | Beck et al. |
| 2018/0214192 | A1 | 8/2018 | Roby et al. |
| 2018/0289504 | A1 | 10/2018 | Arthurs et al. |
| 2018/0325570 | A1 | 11/2018 | Kuntz et al. |
| 2019/0262042 | A1 | 2/2019 | Mari et al. |
| 2019/0125408 | A1 | 5/2019 | Asfora et al. |
| 2019/0133657 | A1 | 5/2019 | Orbay et al. |
| 2019/0231406 | A1 | 8/2019 | Asfora |
| 2019/0239935 | A1 | 8/2019 | Willis et al. |
| 2019/0262048 | A1 | 8/2019 | Sutika |
| 2019/0262049 | A1 | 8/2019 | Tempco et al. |
| 2019/0290341 | A1 | 9/2019 | Loftus |
| 2019/0290342 | A1 | 9/2019 | Lanois et al. |
| 2019/0298528 | A1 | 10/2019 | Lindsey et al. |

OTHER PUBLICATIONS

Australian Government IP Australia, Australia Examination Report No. 1 for application No. 2021232574, dated Oct. 20, 2023, 6 pages.
Canadian Intellectual Property Office, Canadian Office Action for application No. 3,169,917, dated Nov. 7, 2023, 5 pages.
International Searching Authority, International Search Report and Written Opinion of the International Searching Authority, International Application No. PCT/US 21/20592, Jul. 28, 2021, 12 pages, ISA/US.

* cited by examiner

IMPLANT SYSTEM AND METHOD FOR JOINT FUSION

PRIORITY

This present application is a continuation of U.S. patent application Ser. No. 17/190,280, filed Mar. 2, 2021 which claims the benefit of the filing date of U.S. Provisional Patent Application 62/985,036, filed Mar. 4, 2020, and titled, Implant System and Method for Joint Fusion, which is incorporated herein by reference, in its entirety.

FIELD

The present disclosure relates, in some embodiments, to implant systems and methods for joint fusion applications, and more specifically, in some embodiments, to screw systems that treat sacroiliac joint dysfunction.

BACKGROUND

Sacroiliac joint dysfunction is often the result of worn or degenerative cartilage between the sacrum and the iliac bones. The cartilage acts to buffer and absorb loads between the bones, and when it is worn away, the bones begin to rub on each other. Cartilage damage may occur over time for any number of reasons. For example, gait issues, may place uneven pressure on one side of the pelvis causing wear and tear on the SI joint, pregnancy and childbirth can cause sacroiliac joint pain due to instability of ligaments after childbirth, prior lower back surgeries, and activities that place repeated stress on the joint, including contact sports, heavy lifting, or labor-intensive jobs.

One treatment for addressing SI joint pain is sacroiliac joint fusion. This treatment eliminates movement at the sacroiliac joint by fusing together the iliumilium and sacrum. In some instances, sacroiliac fusion employees implanted screws or rods across the joint. Conventional screws and rods are formed of metal for strength, but these can lack the capacity to allow bone growth into and through the implant for true fusion. Accordingly, support for the fusion is maintained primarily by the screw and may not be shared sufficiently with the surrounding bony structure.

The present disclosure may address one or more of the shortcomings of conventional systems.

SUMMARY

The embodiments of the invention are best summarized by the claims that follow the description.

According to example implementations, the present disclosure teaches an implant system for joint fusion. The implant system includes a distal portion having a thread having a first thread minor, a first thread major, and a first pitch. The distal portion may also have a reverse cut, helical fenestration formed through the thread. A middle portion may be adjacent the distal portion and may be devoid of threads. The middle portion may include a porous outer surface structure to promote bony integration. The porous outer surface structure may have a leading end and a trailing end, with the leading end having a diameter larger than the first thread minor. A proximal portion may be adjacent the middle portion and may include a proximal thread having a second thread minor, a second thread major, and a second pitch. The second thread minor may be substantially the same as the trailing end of the middle portion.

In some aspects, the second thread minor is tapered differently than the second thread major. In some aspects, the implant includes a plurality of linear slots disposed radially about the middle portion. In some aspects, the second pitch of the proximal thread is different than the first of the distal thread. In some aspects, the porous outer surface structure of the middle portion is substantially cylindrical from a leading end to a trailing end. In some aspects, the distal portion and the proximal portion are formed of a nonporous material. In some aspects, the middle portion comprises a porous structure formed by a 3D printed lattice structure. In some aspects, the porous structure has a porosity in a range of about 45% to 85%. In some aspects, the implant includes a proximal end, and the proximal portion is tapered outwardly toward the proximal end. In some aspects, the proximal portion comprises a screw head disposed at the proximal end of the implant, the screw head having an outer periphery with the diameter greater than a diameter of the second thread major.

According to additional example implementations, the present disclosure teaches an implant system for joint fusion. The implant system may include a monolithic elongated shaft comprising a distal portion having a thread having a first thread minor, a first thread major, and a first pitch. The shaft may also include a middle portion adjacent the distal portion, with the middle portion having a diameter smaller than a diameter of the first thread minor. The elongated shaft also may include a proximal portion adjacent the middle portion. The proximal portion may include a proximal thread having a second thread minor, a second thread major, and a second pitch, the second pitch being smaller than the first pitch. The implant system also may include a porous sleeve disposed about the middle portion. The porous sleeve may include a porous outer surface structure to promote bony integration. The porous outer surface structure may have a leading end and a trailing end, with the leading end having a diameter larger than the first thread minor.

In some aspects, the distal portion comprises a reverse cut, helical fenestration formed through the thread. In some aspects, the second thread minor is tapered differently than the second thread major. In some aspects, the implant system may include a plurality of linear slots disposed radially about the middle portion. In some aspects, the porous outer surface structure of the middle portion is substantially cylindrical from a leading end to a trailing end. In some aspects, the distal portion and the proximal portion are formed of a nonporous material. In some aspects, the porous sleeve is formed by a 3D printed lattice structure. In some aspects, the implant includes a proximal end, the proximal portion being tapered outwardly toward the proximal end of the implant. In some aspects, the proximal portion comprises a screw head disposed at the proximal end of the implant, the screw head having an outer periphery with the diameter greater than a diameter of the second thread major.

According to additional example implementations, the present disclosure teaches an implant system for joint fusion that includes a distal portion having a distal thread comprising a cylindrical first thread minor, a first thread major, and a first pitch. A middle portion may be adjacent the distal portion and may include a porous outer surface structure to promote bony integration. The middle portion may also include an inner structure more shear resistant than the porous outer surface structure. The porous outer surface structure may have a leading end and a trailing end, with the leading end having a diameter larger than the first thread minor. A proximal portion may be disposed adjacent the middle portion. The proximal portion may include a proximal thread having a second thread minor, a second thread major, and a second pitch. The proximal portion may have a leading end, and the second thread minor may substantially match a diameter of the trailing end of the middle portion. The proximal portion may taper outwardly from the leading end of the proximal portion to the trailing end of the proximal portion.

In some aspects, the second thread minor is tapered differently than the second thread major. In some aspects, the implant system may include a plurality of linear slots disposed radially about the middle portion. In some aspects, the porous outer surface structure of the middle portion is substantially cylindrical from a leading end to a trailing end. In some aspects, the proximal portion comprises a screw head disposed at the trailing end of the proximal portion, the screw head having an outer periphery with the diameter greater than a diameter of the second thread major.

According to additional example implementations, the present disclosure teaches an implant method that may include drilling a hole in a first bone segment and in a second bone segment, the bone segments forming a joint, and introducing an implant to the hole so that the distal portion is threadably secured in the first bone segment and the proximal portion is threadably secured in the second bone segment, and the middle portion intersects the joint of the first bone segment in the second bone segment.

According to additional example implementations, the present disclosure teaches an implant system for joint fusion that may include distal, middle, and proximal portions. The distal portion may have a hollow bore and a thread having a first thread minor, a first thread major, and a first pitch. The distal portion also may have a reverse cut, helical fenestration formed through the thread and intersecting the hollow bore. The middle portion may be adjacent the distal portion and may be devoid of threads and may include a porous outer surface structure to promote bony integration. The porous outer surface structure may have a porosity with a range of about 30-80%. The porous outer surface structure may have a leading end and a trailing end and may being substantially cylindrically shaped from the leading end to the trailing end. The leading end may have a diameter larger than the first thread minor. The proximal portion may be disposed adjacent the middle portion and may include a proximal thread having a second thread minor, a second thread major, and a second pitch. The second thread minor may be substantially the same as the trailing end of the middle portion. The second thread minor may be tapered differently than the second thread major, and the second pitch may be in a range of about 60-90% of the first pitch of the thread of the distal portion. The middle portion and the proximal portion may have a plurality of linear slots radially disposed therein in communication with the hollow bore. Each slot of the plurality of linear slots may extend in a substantially axial direction.

In some aspects, the middle portion comprises a porous structure formed by a 3D printed lattice structure. In some aspects, the proximal portion is tapered outwardly in a proximal direction. In some aspects, the proximal portion comprises a screw head disposed at a trailing end of the proximal portion, the screw head having an outer periphery with the diameter greater than a diameter of the second thread major.

According to additional example implementations, the present disclosure teaches a surgical instrument set that may include a drill tube having a distal end and a proximal end, with one or more anchoring devices disposed thereon. The surgical instrument also may include a striker tube laterally insertable over the proximal end of the drill tube. The striker tube may include a main body and a sliding collar, with the sliding collar being displaceable to lock and unlock the striker tube from the drill tube.

In some aspects, the drill tube comprises an external surface with a cutout formed therein the cutout being sized to receive a displaceable portion of the striker tube. In some aspects, the drill tube comprises one of a flange and a recess, the drill tube comprising a striker tube comprising the other of the flange and the recess, the flange and the recess sized to mate to transfer loading on the striker tube through the flange and recess to the drill tube.

Additional example implementations are directed to surgical techniques and methods. Others are directed to striker tubes. Yet others are directed to parallel guide plates. Others are also contemplated.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Figure 1:
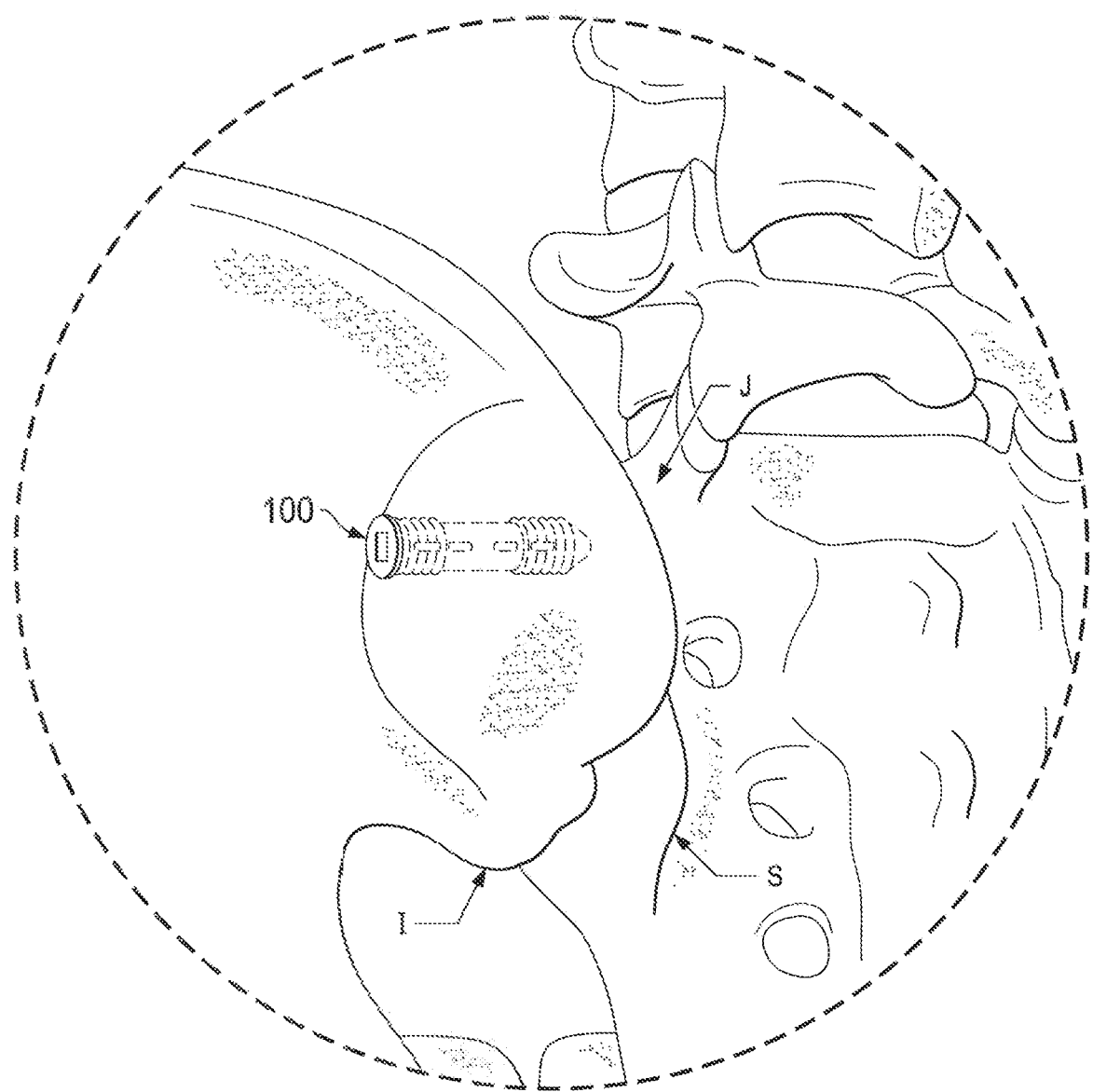
FIG. 1 illustrates a perspective illustration of a sacroiliac joint with an implant disposed therein, according to some example implementations of the present disclosure.

Embodiments of the present disclosure and their advantages are described in the detailed description that follows. It should be appreciated that like reference numerals are used to identify like elements illustrated in one or more of the figures for purposes of illustrating but not limiting embodiments of the present disclosure.

DETAILED DESCRIPTION

In the following description, specific details describe some embodiments consistent with the present disclosure. Numerous specific details are set forth in order to provide a thorough understanding of the embodiments. It will be apparent to one skilled in the art, however, that some embodiments may be practiced without some or all of these specific details. The specific embodiments disclosed herein are meant to be illustrative but not limiting. One skilled in the art may realize other elements that, although not specifically described, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional. In some instances, well known methods, procedures, and features have not been described in detail so as not to unnecessarily obscure aspects of the embodiments.

The present disclosure provides a solution to fixating a bone joint, such as the sacroiliac joint. It includes an implant particularly suited for passage through the ilium, spanning the SI joint, and embedding in the sacrum. In some implementations, the implant is manufactured using a 3D printing method that provides a midshaft porous region that may accommodate bone ingrowth, and a secure, patient-friendly solution for sacroiliac joint fixation. Furthermore, the shape, size, and design features described herein may provide for additional purchase across the joint to promote strength and healing.

FIG. 1 illustrates a sacroiliac joint with an implant disposed therein. Particularly, FIG. 1 shows a sacrum S and an ilium I forming an SI joint J therebetween. The SI joint J may typically include cartilage or tissue between the sacrum S and the ilium I. In some instances, the cartilage or tissue may have been worn away or surgically removed so that the sacrum S and the ilium I about directly against each other. An implant 100 is disposed laterally across the SI joint J, to fix the ilium I to the sacrum S. Although a single implant 100 is shown in FIG. 1, other implementations may include multiple implants 100 implanted adjacent to each other, with each spanning the SI joint J, to provide sufficient strength to the SI joint J.

Figure 2:
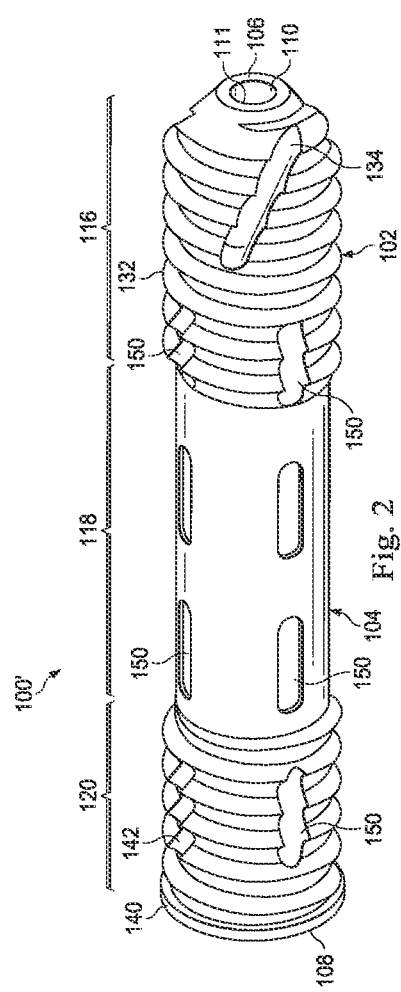
FIG. 2 is a perspective illustration of an implant according to some example implementations of the present disclosure.
Figure 3:
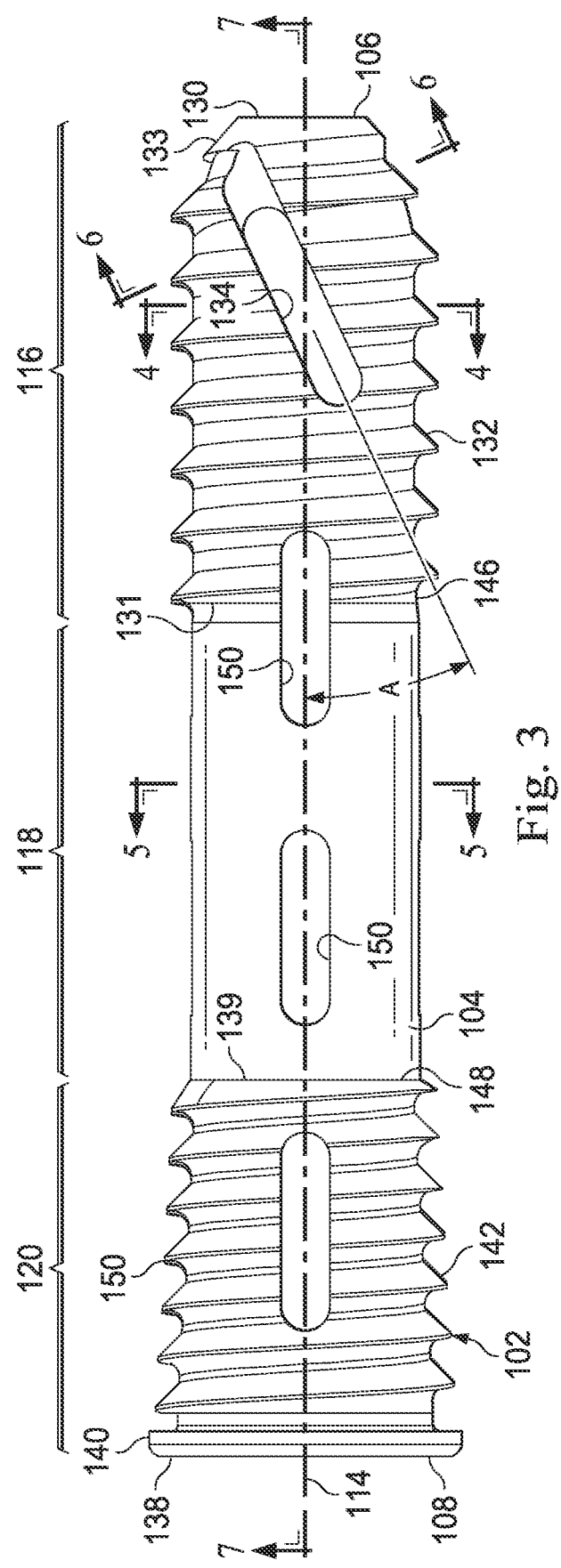
FIG. 3 is a plan view of another implant according to some example implementations of the present disclosure.

FIGS. 2-7 show different features of the implant 100. FIG. 2 shows a first implant 100', and FIGS. 3-7 show a second implant 100 that is similar in all major features to the implant 100', except that the implant 100' in FIG. 2 is longer in length and includes additional linear slots as described below. The implants 100' and 100 are particularly shaped and configured to fuse two bone segments across a joint. For clarity, this disclosure will reference the implant 100. In the implementation shown, the implant 100 is a screw designed to engage and secure one bone structure to the other. As indicated above, one example joint that may be fused with the implant 100 is the sacroiliac joint. However, the implant may be used in other implementations to fuse across other joints in a patient. The implant 100 is formed of a hollow elongated shaft 102 and a porous sleeve 104 disposed about a middle portion of the elongated shaft 102. In the example shown, the implant 100 is fenestrated through both the elongated shaft 102 and the porous sleeve 104. The fenestrated implant 100 may allow bone growth to occur through the implant.

The implant 100 may be formed of any suitable product or material, and in some implementations may be formed using a 3D printing process. In 3D printed implementations, the implant 100 may be formed of a biocompatible material having suitable strength to fuse a joint, such as an SI joint. Some examples of the implant 100 are 3D printed using titanium, steel, or other biocompatible metal materials, including alloys. Other examples of the implant 100 are 3D printed using reinforced or unreinforced polymeric materials or ceramics, among others. In the description herein, both the elongated shaft 102 and the porous sleeve 104 may be simultaneously printed during the same process, and in some implementations form a single monolith. Accordingly, in some implementations the distinction between the elongated shaft 102 and the porous sleeve 104 is solely based on the porosity differences between the elongated shaft 102 on the porous sleeve 104. For example, the elongated shaft may be substantially nonporous and the porous sleeve 104 may be porous in a manner promoting bony ingrowth. In yet other implementations, the elongated shaft 102 is formed separately and independently of the porous sleeve 104, and the porous sleeve may be applied about the elongated shaft 102. In such implementations, the elongated shaft 102 and the porous sleeve 104 may be fully distinct components, brought together to form the implant 100. The material of the elongated shaft 102 may be selected to have sufficient strength to bear shear loads applied by opposing bone structure forming adjacent sides of a joint. Although any 3D printing method may be used, in some implementations, either the elongated shaft 102, the porous sleeve 104, or the implant 100 as a whole may be printed using a powder bed fusion process. In some implementations, the implant is formed of a biocompatible metallic material for their strength and characteristics of promoting bone fusion.

The elongated shaft 102 may extend between a distal end 106 and a proximal end 108. In the implementation shown, the elongated shaft 102 is cannulated such that a hollow bore 110 extends through the distal end 106, the length of the elongated shaft 102 and through the proximal end 108. The hollow bore 110 may be defined by inner surfaces of the elongated shaft 102 and may include a first inner width W1 extending through substantially the entire elongated shaft 102, with a second inner width W2 forming a bore opening 111 at the distal end 106. In the example shown, the second inner width W2 is smaller than the first inner width W1. In some implantation techniques described herein, the second inner width W2 may be sized to provide a close clearance fit about a guide pin, while the first inner width W1 is sized to accommodate all graft or autograft between the outer surface of a guide pin and the inner surfaces defining the hollow bore 110. In the implementation shown, the second inner width W2 is substantially cylindrical and extends from a location directly adjacent the distal end 106 toward the proximal end 108. In some implementations, the second inner width W2 may increase or decrease, such as, for example, if the region shown as the second inner width W2 may taper or become narrower as it extends toward the distal end 106. In this implementation, the hollow bore 110 includes a drive bore 112 having a third inner width W3 sized equal to or greater than the second inner width W2. In the implementation shown, the third inner width W3 is sized larger than the second inner width W2. In some implementations, the drive bore 112 may be shaped and formed to engage a driving instrument, such as a surgical screwdriver that may be used to screw or otherwise drive the implant 100 to a desired location across a joint during a surgical implantation procedure. For example, the drive bore 112 may be square shaped, rectangular shaped, star-shaped, or may have yet another shape particularly configured to mate with the driving instrument, such as the surgical screwdriver. In some implementations, the surfaces forming the first inner width W1 and the second inner width W2 may be substantially cylindrical. The hollow bore 110 may define a longitudinal axis 114.

In the implementation shown, the elongated shaft 102 may be divided into a distal portion 116, a middle portion 118, and a proximal portion 120. In the implementation shown, the distal portion 116 extends from the distal end 106 to the middle portion 118, and the proximal portion 120 extends from the proximal end 108 to the middle portion 118. In this implementation, the distal portion 116 and the proximal portion 120 are threaded portions, while the middle portion 118 is devoid of threads and circumscribed by the porous sleeve 104. Furthermore, in the implementation shown, the distal portion 116 may have an axial or longitudinal length larger than an axial or longitudinal length of the proximal portion 120.

The distal portion 116 forms a leading end of the elongated shaft 102 and extends between a distal portion leading end 130 at the distal end 106 of the implant 100 to a distal portion trailing end 131. The distal portion 116 may incorporate a taper 133 at the distal portion leading end 130 to aid in guiding the implant 100 when introduced to a pilot hole formed in the bone to be treated. The tapered distal portion leading end 130 angles toward the distal end 106. Extending from the tapered distal portion leading end 130, the distal portion 116 may include a distal thread 132. In the example shown, the distal thread 132 may include a constant thread major, a constant thread minor, and a constant pitch, and the distal thread 132 may extend from the distal end 106 along substantially the entire length of the distal portion 116. Consistent with the description of the constant thread minor, the diameter of the distal portion 116 at the thread minor is substantially constant such that the outer diameter of the distal portion 116 absent the protruding distal thread 132, is substantially cylindrical, except for the tapered distal portion leading end 130. As used herein, the thread major refers to the major or largest material diameter of the thread, and the thread minor refers to the minor or smallest material diameter of the thread.

Figure 4:
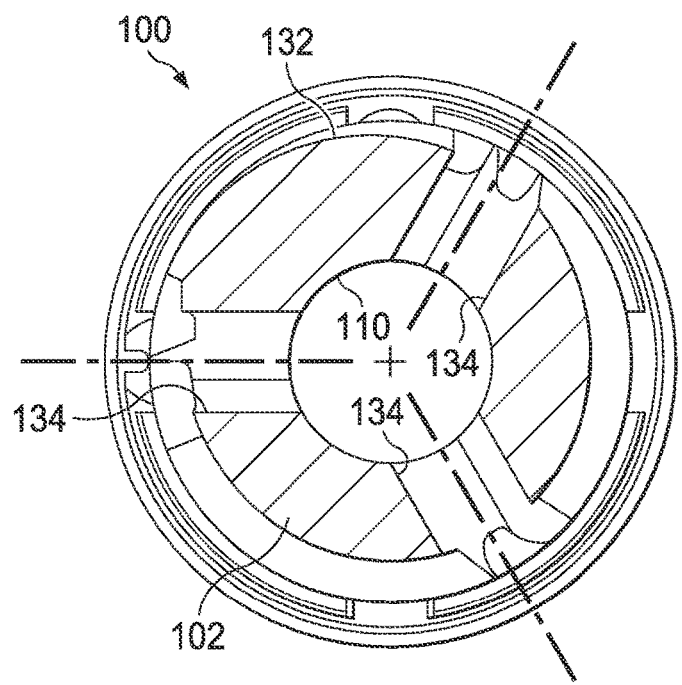
FIG. 4 is a cross-sectional view taken along lines 4-4 of the implant of FIG. 3 according to some example implementations of the present disclosure.
Figure 5:
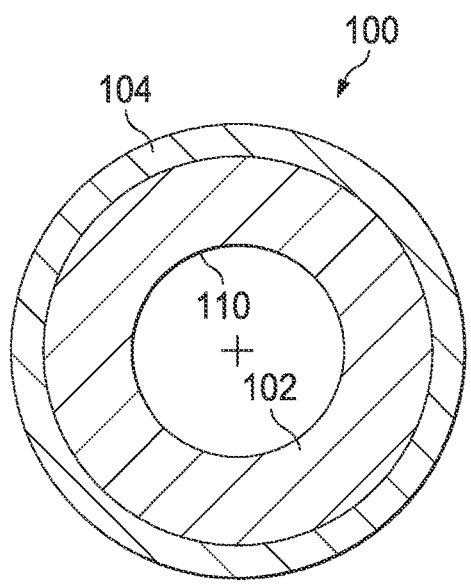
FIG. 5 is a cross-sectional view taken along lines 5-5 of the implant of FIG. 3 of an implant according to some example implementations of the present disclosure.
Figure 6:
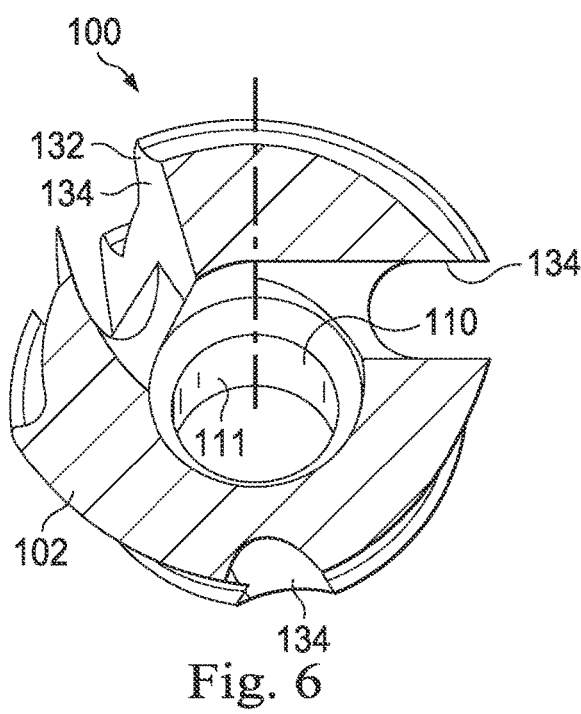
FIG. 6 is a cross-sectional view taken along lines 6-6 of the implant of FIG. 3 of an implant according to some example implementations of the present disclosure.

A plurality of helical fenestrations 134 are disposed in the distal portion 116. In the example shown, the helical fenestrations 134 are spaced from the distal end 106, but may begin within the tapered distal portion leading end 130 of the distal portion 116 and may terminate along the distal portion 116 in the region of the constant diameter portion of the thread minor. Accordingly, the helical fenestration 134 may have an axial length that both begins and terminates in the distal portion 116. The helical fenestrations 134 are reverse cut with respect to the distal thread 132 and cross at least three threads of the distal thread 132. Although disclosed as crossing at least three threads of the distal thread 132, some embodiments may include helical fenestrations 134 that cross one or two distal threads, or four or more distal threads. In the example shown, the helical fenestrations 134 may be angled from the longitudinal axis 114, at an angle A within a range of about 10 to 40°. In some implementations, the angle A is in a range of about 20 to 30°, and in one implementation, the angle A is about 25°. FIG. 4 shows a cross-sectional view of the implant 100 through the distal portion including the helical fenestrations 134. As shown, the helical fenestrations penetrate through the elongated shaft to the hollow bore 110. The helical fenestrations 134 are particularly configured to form bone harvesting fenestrations. Accordingly, as the implant 100 is threaded into the bone, the distal thread 132 (labeled in FIG. 7 as 132') adjacent the helical fenestrations 134 that projects radially outwardly from the thread minor, may penetrate the bone structure and may cut or carve the bone structure such that some autograft material may be introduced into the helical fenestrations 134 and into the hollow bore 110. That is, the helical fenestrations 134, through the distal threads 132, may carve autograft bone which may reside in the helical fenestrations and the hollow bore 110 to promote bone growth into the helical fenestrations and the hollow bore 110 of the implant 100. As best seen in FIG. 5, the implementation shown includes three helical fenestrations 134. Other implementations include one, two, or more than three helical fenestrations 134.

The proximal portion 120 forms a trailing end of the elongated shaft 102 and extends between a proximal portion trailing end 138 and a proximal portion leading end 139. The proximal portion trailing end 138 may include a low-profile screw head 140, and the proximal portion 120 may include a proximal thread 142. The screw head 140 may be disposed at the proximal end 108 of the elongated shaft 102. The screw head 140 may have a width larger than a width of any other portion of the implant 100. In the implementation shown, the screw head 140 may have a cylindrical periphery 144 with a chamfer or round connecting the cylindrical periphery 144 to the proximal end 108 to prevent soft-tissue irritation. Here, the proximal thread 142 includes a tapered thread major and a tapered thread minor. In some implementations, the taper of the thread minor is different than the taper of the thread major. As a result, the thread depth may increase or decrease over the length of the proximal portion 120. For example, the taper of the thread minor in the proximal portion 120, as measured from the longitudinal axis 114 may be in a range of about 1 to 4° in some implementations, and in a range of about 1.5 to 2.5° in some implementations, and in a range of about 2.0 to 2.1° in some implementations, and about 2.1° in some implementations. In a similar manner, the taper of the thread major in the proximal portion 120, as measured from the longitudinal axis 114, may be in a range of about 0.9 to 3.9° in some implementations, and in a range of about 1.4 to 2.4° in some implementations, and about 1.9 to 2.0° in some implementations, and about 2.0° in some implementations. Additional taper ranges are contemplated. Accordingly, in some implementations, the taper of the thread major may be smaller than the taper of the thread minor. In addition, the proximal thread 142 includes a pitch smaller than the pitch of the distal thread 132. In some implementations, the pitch of the proximal thread 142 is in a range of about 60% to 90% of the pitch of the distal thread 132, although additional pitch ranges are contemplated.

The middle portion 118 of the elongated shaft 102 may have a middle portion leading end 146 and a middle portion trailing end 148. In some implementations, the middle portion of the elongated shaft 102 may considered to have two elements: The middle portion of the elongated shaft 102 and the porous sleeve around the middle portion of the elongated shaft. Without the porous sleeve 104, the middle portion 118 may have an outer diameter smaller than both the thread minor of the distal portion 116 and the thread minor of the proximal portion 120. With the porous sleeve 104, the middle portion 118 may have an outer diameter larger than the thread minor of the distal portion 116 and the same as the starting thread minor of the proximal portion 120. In this implementation, the middle portion 118 of the elongated shaft 102 is formed as a monolith, having substantially the same density properties as the distal portion 116 and the proximal portion 120. Structuring the distal portion 116, the middle portion 118, and the proximal portion 120 of the elongated shaft 102 in this manner may provide structural integrity to the implant 100 to help carry loads applied to a joint, such as a sacroiliac joint where the implant 100 may reside.

The porous sleeve 104 may be 3D printed with a desired porosity that promotes ingrowth using a lattice structure that promotes bony fusion with the implant 100. As indicated herein, some implementations of the porous sleeve 104 may be 3D printed simultaneously with the elongated shaft 102, and the porous sleeve 104 and elongated shaft 102 may form a monolith, and may be formed of the same material. In yet other implementations, the porous sleeve may be printed simultaneously with the elongated shaft 102, and the porous sleeve 104 and elongated shaft 102 may form distinct and separate components that make up the implant 100. In yet other implementations, the porous sleeve 104 may be printed separately and apart from the elongated shaft 102, and may be applied about the shaft 102 to form the implant 100.

The porous sleeve 104 may form a porous outer surface structure disposed about the middle portion 118 and may extend the entire length of the middle portion 118 from the middle portion leading end 146 to the middle portion trailing end 148. Because of this, the porous sleeve 104 may be disposed directly adjacent, such as abutting up against the distal portion trailing end 131 and the proximal portion leading end 139. As such, the porous sleeve 104 may abut against material forming the thread minor of the distal thread 132 and against material forming the thread minor of the proximal thread 142. Accordingly, as shown in the cross-sectional view of FIG. 5, the middle portion 118 is a two-layered structure which includes an inner solid core of the elongated shaft 102 with the outer porous sleeve 104 disposed around the inner solid core. The inner core of the elongated shaft 102 in the middle portion 118 may provide sufficient desired mechanical strength to support loads applied at or across the joint being treated, while the porous sleeve 104 may promote bony integration and healing. In some implementations, the porosity of the porous sleeve 104 is in the range of 30% to 80% of the porosity of the elongated shaft 102, and the thickness of the porous sleeve 104 may be in a range of about 0.3 mm to 1.5 mm, depending on the size and application of the implant 100. In some implementations, the porosity of the porous sleeve 104 is in the range of about 45% to 85%. In some implementations, the thickness of the porous sleeve may be in a range of about 0.010 mm to 2 mm thick. In some implementations, the thickness of the porous sleeve may in a range of about 0.015 to 0.5 mm thick. Depending on the application, the thickness of the porous sleeve may be between about 8% to 100% of the thickness of the solid core of the middle portion 118. In some embodiments, the thickness of the porous sleeve is about 20 to 40% of the thickness of the underlying elongated shaft. For example, in some embodiments, the thickness of a wall of the porous shaft is about 0.2 to 0.25 mm and the thickness of the underlying solid wall of the elongated shaft is about 0.7 to 0.8 mm.

In the implementation shown, the porous sleeve 104 has a constant major diameter extending from one end to the other. The major diameter of the porous sleeve 104 (and therefore the major diameter of the middle portion 118) may be larger than the thread minor of the distal thread 132. This size differential may create a press fit between the porous sleeve 104 forming the middle section and surrounding bones when implanted. Clinically, this press fit may provide better implant-to-bone contact and may therefore improve initial fixation and better bony integration during fusion than conventional systems.

In addition, the starting thread minor of the proximal thread 142 is substantially the same as the major diameter of the porous sleeve 104, and in some implementations, may be substantially identical to the major diameter of the porous sleeve 104. Since the proximal thread 142 is tapered, this radial compression/press fit feature may extend to the proximal portion 120 for improved fixation over conventional systems. In some implementations, the major diameter of the porous sleeve 104 is in a range of about 0.01 to 0.1 mm larger than the minor diameter of the distal thread. In one implementation, the major diameter of the porous sleeve 104 is about 2 mm larger than the minor diameter at the distal thread. The minor diameter of the proximal thread 142 may start at about the same size as the major diameter of the porous sleeve 104. As indicated herein, the minor diameter of the distal portion 116, the diameter of the middle portion 118, and the starting minor diameter of the proximal portion 120 give a continuous press fit between the implant 100 and a bone interface for better initial fixation and joint fusion.

Figure 7:
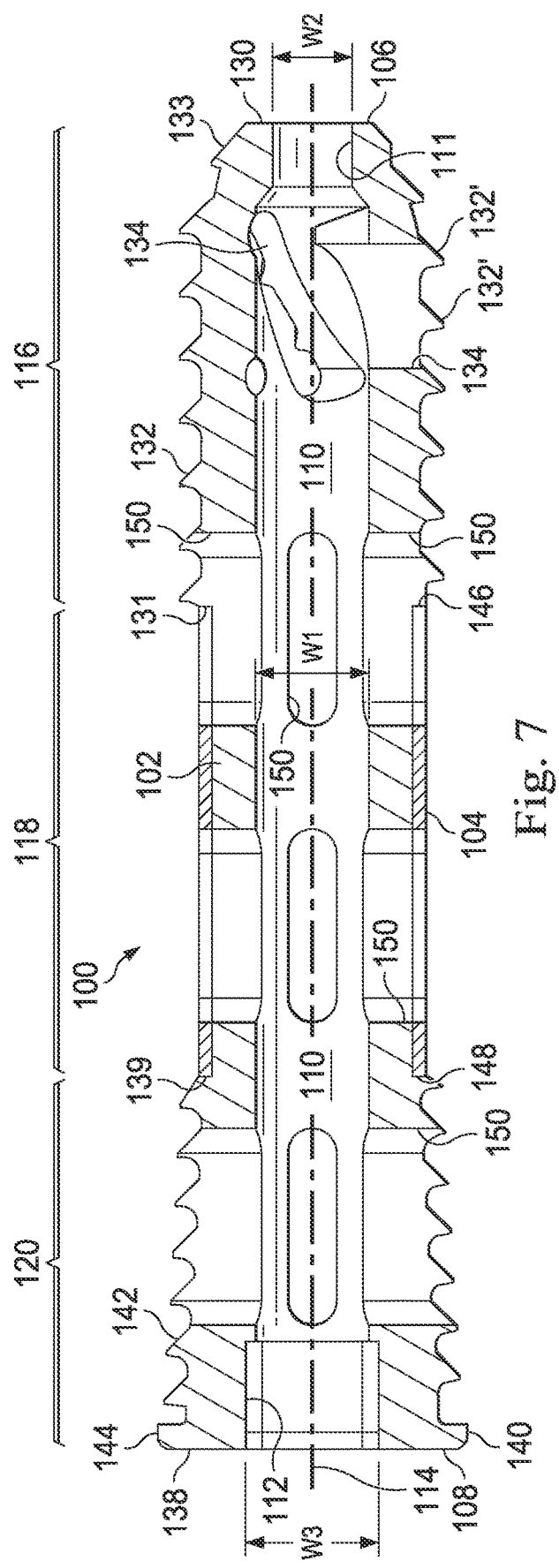
FIG. 7 is a cross-sectional view taken along lines 7-7 of the implant of FIG. 3 of an implant according to some example implementations of the present disclosure.

The implant 100 may include a plurality of axially extending, linear slots 150 in communication with the hollow bore 110, as can be seen in FIG. 7. The linear slots extend through both the elongated shaft 102 and the porous sleeve 104 to facilitate bony ingrowth into the hollow bore 110. In the example shown, the linear slots 150 are all disposed proximal of the helical fenestrations 134, with a distal-most linear slot 150 axially displaced from the helical fenestrations 134.

Also, in the example shown, the linear slots 150 are disposed in the distal portion 116, the middle portion 118, and the proximal portion 120. In yet other implementations, the linear slots 150 are formed only in the proximal portion 120 and the middle portion 118. While the helical fenestrations 134 may promote bone harvesting as described herein, the linear slots 150 may promote bone growth through graft material packed into the hollow bore before, during, or after implantation. In the example shown, the linear slots 150 are radially spaced about the implant 100 by 90°, and as such, the implant 100 includes four linear slots 150 at each level. As used herein, a level is a plurality of linear slots 150 that are aligned along the longitudinal axis 114. Accordingly, the example shown in FIGS. 3-7 has three levels.

FIGS. 8A to 8F show an exemplary surgical technique for implanting the implant 100 across a joint to achieve joint fixation. In the example implementations described herein, the technique uses a minimally invasive lateral approach to deliver the implant 100.

Figure 8A:
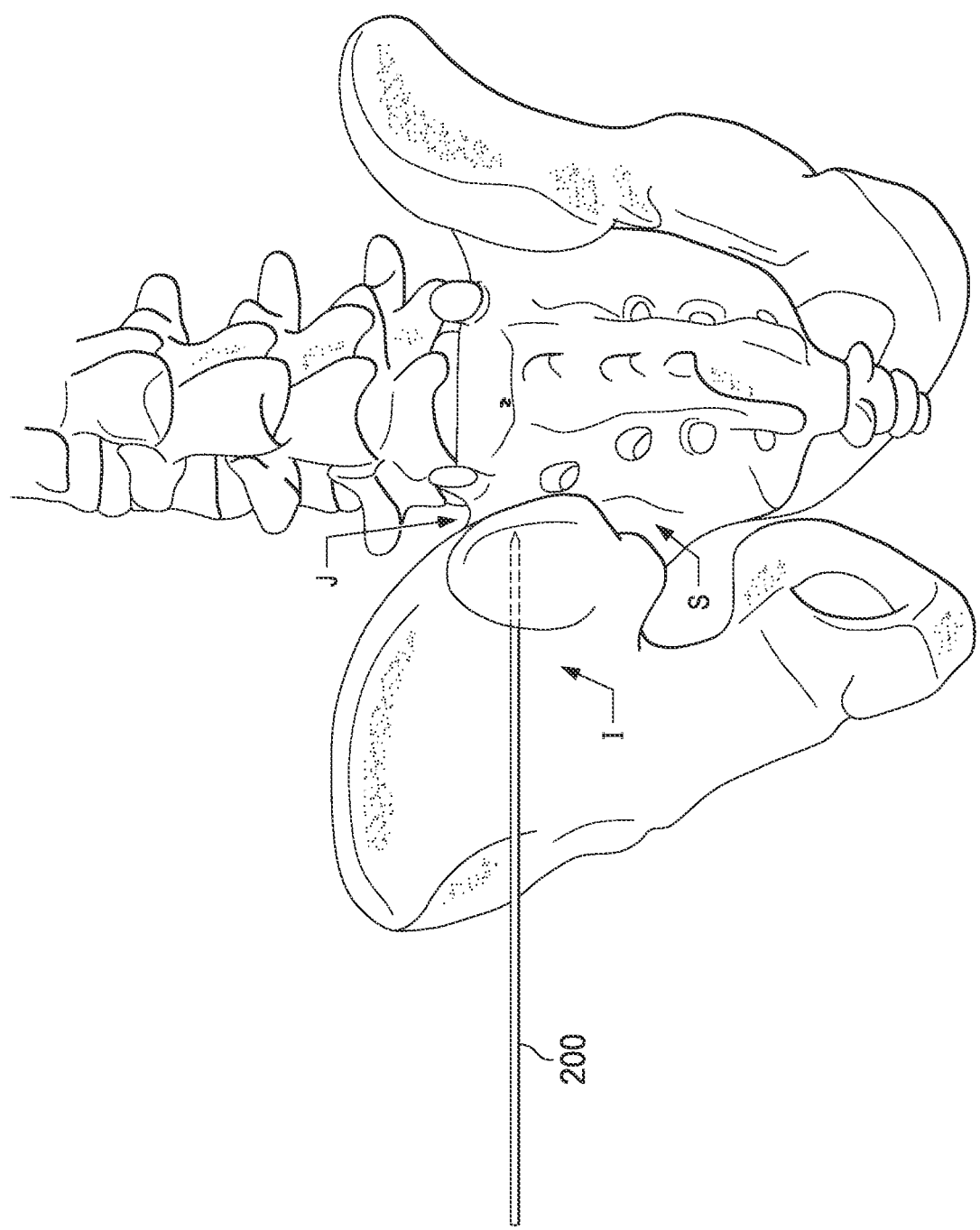
FIG. 8A is a perspective view of a skeletal structure including the sacroiliac joint undergoing a surgical technique according to some example implementations of the present disclosure.

FIG. 8A shows the example sacrum S and ilium I forming the SI joint J. The surgical method may begin by a healthcare provider advancing a guide pin 200, such as a Steinmann pin, through the ilium I and across the SI joint J. Some implementations may employ a second, a third, and a fourth guide pin inserted through the sacral wall of the sacrum S to provide guidance and stability for the insertion of additional implants. The guide pins for the additional implants may be inserted into the ilium I, across the SI joint J, and into the sacrum S one pin at a time before proceeding to tissue dissection, drill guide insertion, and implant insertion, or two to four pins before proceeding to tissue dissection, drill guide insertion, and implant insertion.

Figure 13:
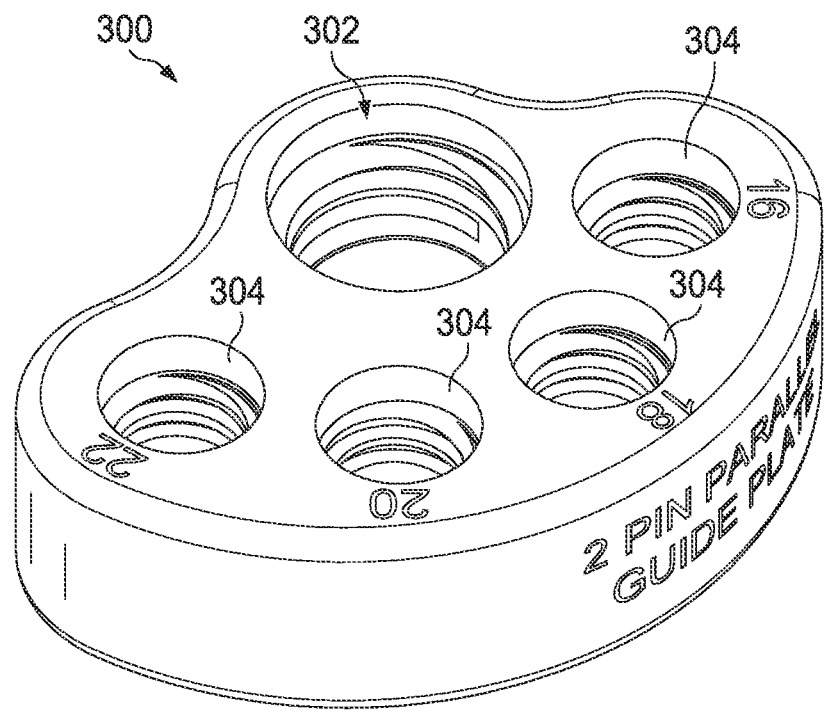
FIG. 13 is a perspective illustration of a surgical instrument according to some example implementations of the present disclosure.
Figure 14:
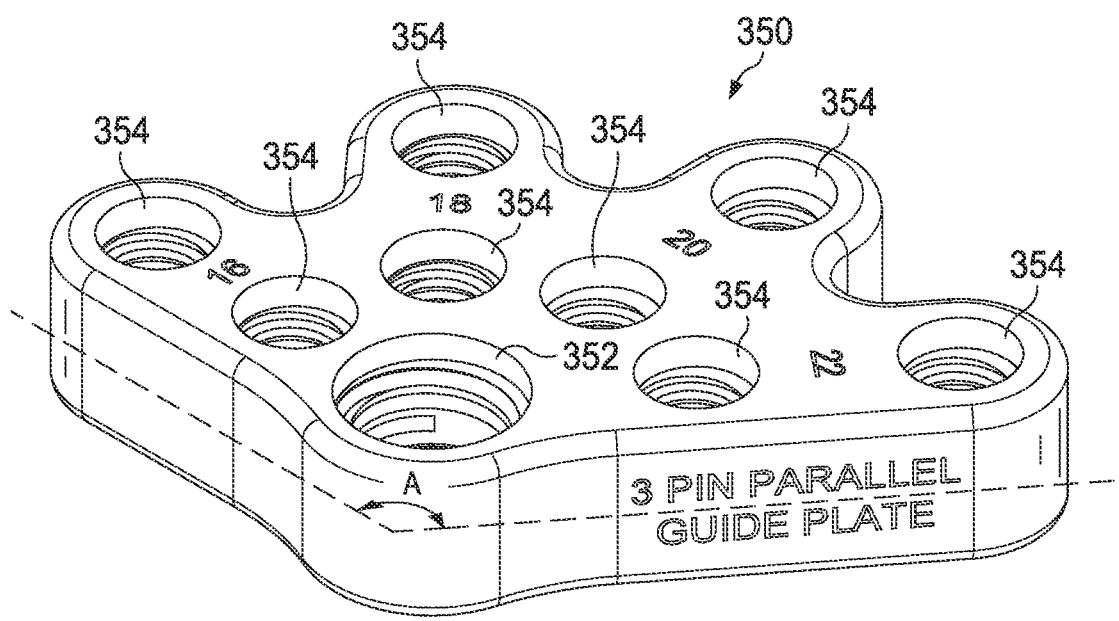
FIG. 14 is a perspective illustration of a surgical instrument according to some example implementations of the present disclosure.

In implementations where more than one implant may be desired, the health care provider may utilize a parallel guide plate to help ensure the implants are properly spaced and positioned. FIG. 13 shows an example two-pin guide plate 300 that may help align multiple implants during a surgical procedure, and FIG. 14 shows an example three-pin guide plate 350 that may help align multiple implants. Referring to FIG. 13, the guide plate 300 is a fixed block of material containing a guide tube hole 302 and four offset holes 304. Each offset hole 304 has a different offset distance from the guide tube hole 302, as indicated by the indicia in FIG. 13. Here, the indicia indicates example offset distances of 16, 18, 20, and 22 units of measurement. In some examples, the units of measurements are millimeters, but other units of measurement are contemplated. In use, a first tube is introduced to the guide tube hole 302, and a second tube is introduced to an offset hole 304 having the desired offset from the first implant location. In this condition, the first and second tubes are parallel and extend perpendicularly from the guide plate 300 along the axes defined by the respective holes. The first tube may then be introduced over the implanted guide pin 200. So doing aligns the second tube the offset distance from the guide pin 200, and a second guide pin can be introduced to the bone through the second tube. As such, the guide plate 300 helps align the guide pins in a parallel manner at a desired distance from each other. In some implementations, the guide plate 300 and the tubes are formed of a radiolucent material so that the guide pin 200 and any additional guide pins may be properly seen during imaging without interference from the tubes or the guide plate 300. Other embodiments are not formed of radiolucent materials. Some suitable example radiolucent materials include polyaryletherketone (PAEK) including polyetheretherketone (PEEK), polyoxymethylene (POM), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, or combinations thereof.

FIG. 14 shows a three-pin guide plate 350 that operates in a manner similar to the two-pin guide plate 300 described above. However, the guide plate 350 may accommodate an additional implant by enabling placement of an additional guide pin so as to form three guide pins in a linear row. The guide plate 350 is a fixed block of material containing a guide tube hole 352 and eight offset holes 354. The offset holes 354 are shown in pairs of two, with each pair positioned to be in a line that intersects with the guide tube hole 352. Accordingly, the lin may intersect the centerlines of the holes 352 and 354. As described above, the holes are spaced a distance apart as indicated by the indicia on the guide plate 350. Here again, the indicia indicates example offset distances of 16, 18, 20, and 22 units of measurement. Both the guide plate 300 and the guide plate 350, include a curved outer wall portion concentric with the respective guide tube holes 302, 352, and sides extending therefrom that extend at angle A less than 180 degrees, and in a range in about 90 to 175 degrees. This permits a broad range of manipulation to align the desired offset holes in a manner desired for a particular procedure. The description below refers to a single implant recognizing that multiple implants could be utilized.

Figure 8B:
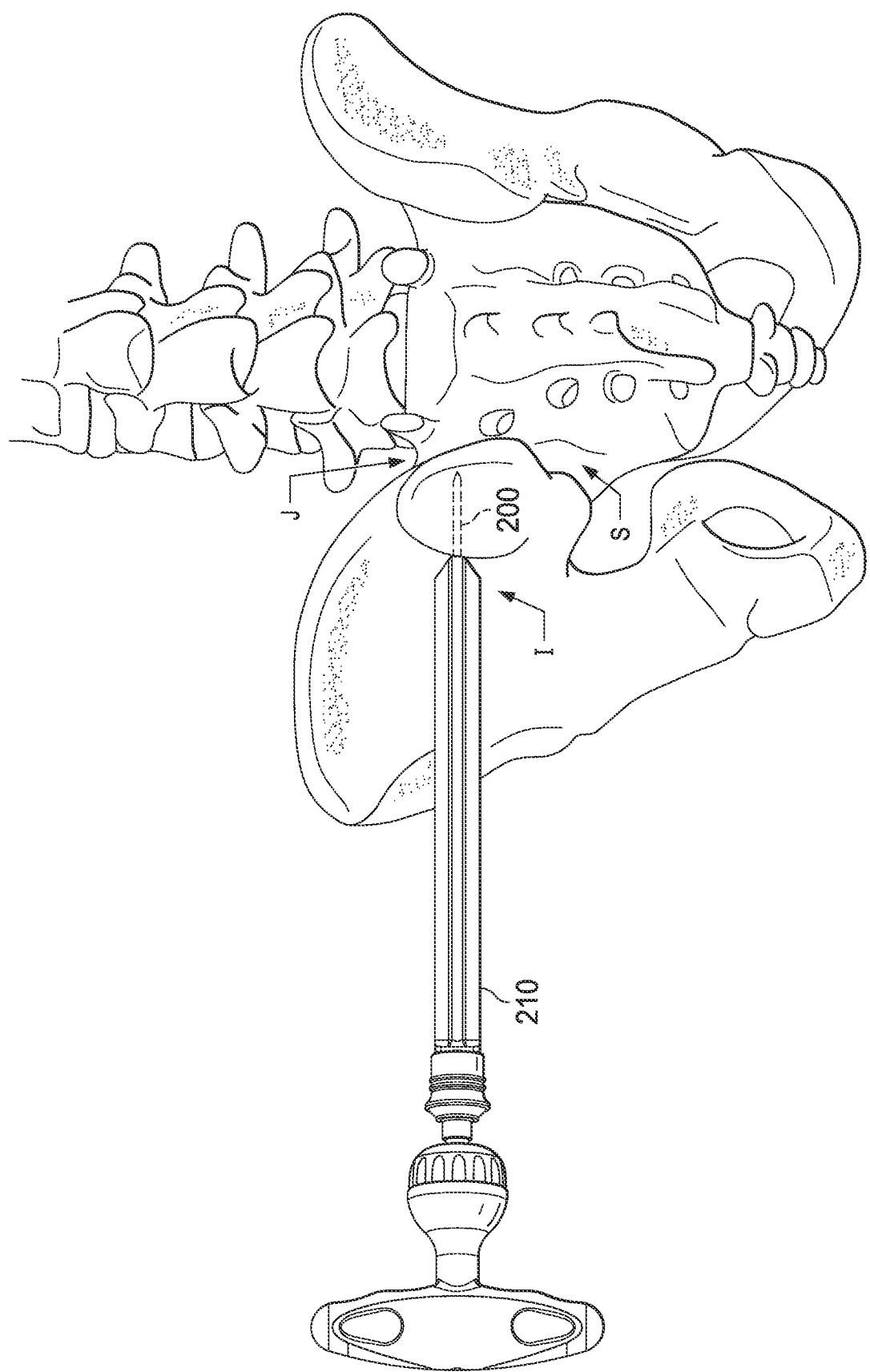
FIG. 8B is a perspective view of a skeletal structure including the sacroiliac joint undergoing a surgical technique according to some example implementations of the present disclosure.
Figure 8C:
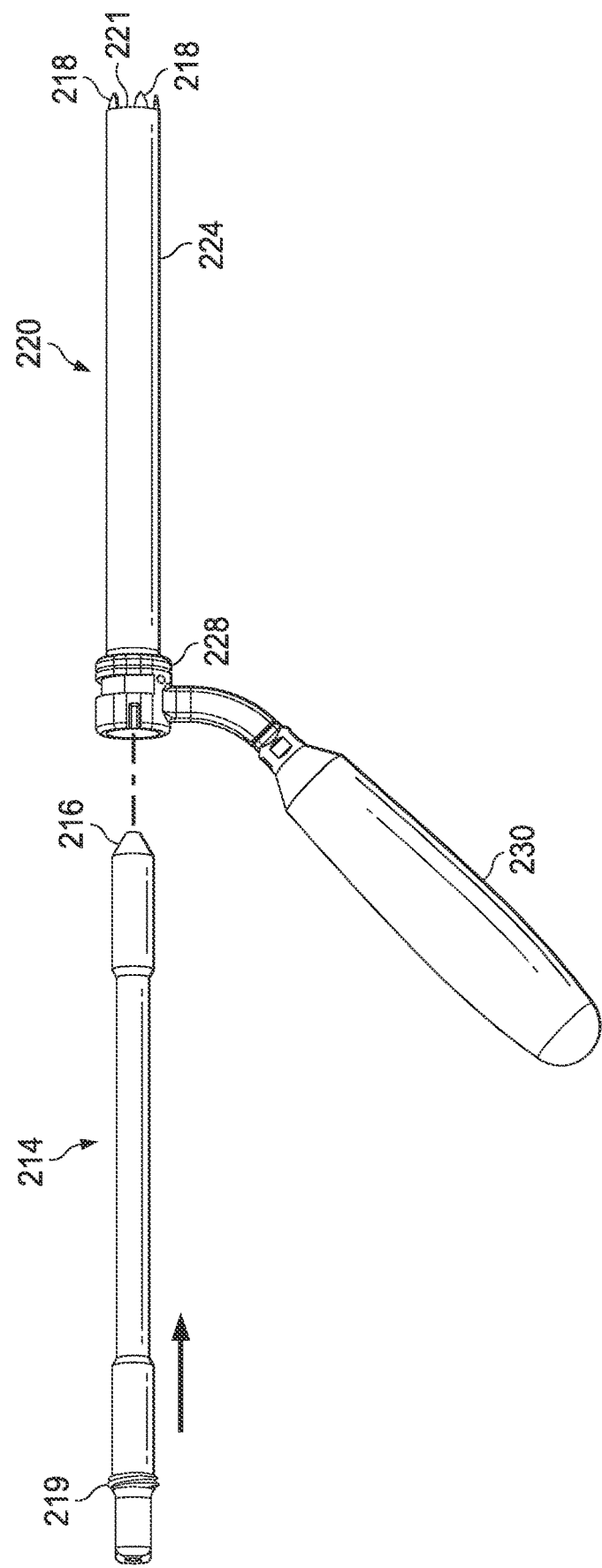
FIG. 8C is a perspective view of example surgical instruments according to some example implementations of the present disclosure.

FIG. 8B shows a tissue dissector 210 used to dissect the soft-tissue down to the ilium I prior to inserting a drill guide 220 (FIG. 8C). In this implementation, the tissue dissector 210 may be inserted over the guide pin 200 until the tip of the tissue dissector is firmly against the ilium I. The tissue dissector 210 may be rotated to release soft tissue surrounding the guide pin.

After removing the tissue dissector 210, the healthcare provider may prepare to introduce the drill guide 220 to the patient. In some implementations, the healthcare provider may assemble a pin sleeve 214 and the drill guide 220 by inserting the pin sleeve 214 into the drill guide 220 in a manner shown in FIG. 8C. Threads 219 of the pin sleeve 214 may engage and thread with threads on the inner portion of the drill guide 220, such as inner threads at the proximal end of the drill guide 220. When assembled, a tapered tip 216 of the pin sleeve 214 will protrude from a distal end 221 of the drill guide 220. With a handle 230 pointing down, the drill guide-pin sleeve assembly may be introduced over the guide pin 200 until the distal tip 216 of the pin sleeve 214 is firmly against the ilium. The pin sleeve 214 may help push tissue to the sides to reduce the chance of catching tissue on spikes 218 of the drill guide 220, in an effort to mitigate additional tissue trauma. With the drill guide 220 introduced to the patient, the pin sleeve 214 may be unthreaded from the drill guide 220 and removed, and leaving the distal tip 221 of the drill guide 220 engaged against the ilium I. Some drill guides 220 may include anchoring elements, such as spikes 218 at the distal end 221 to be penetrate the ilium I, and secure the drill guide 220 in place relative to the ilium I.

Figure 8D:
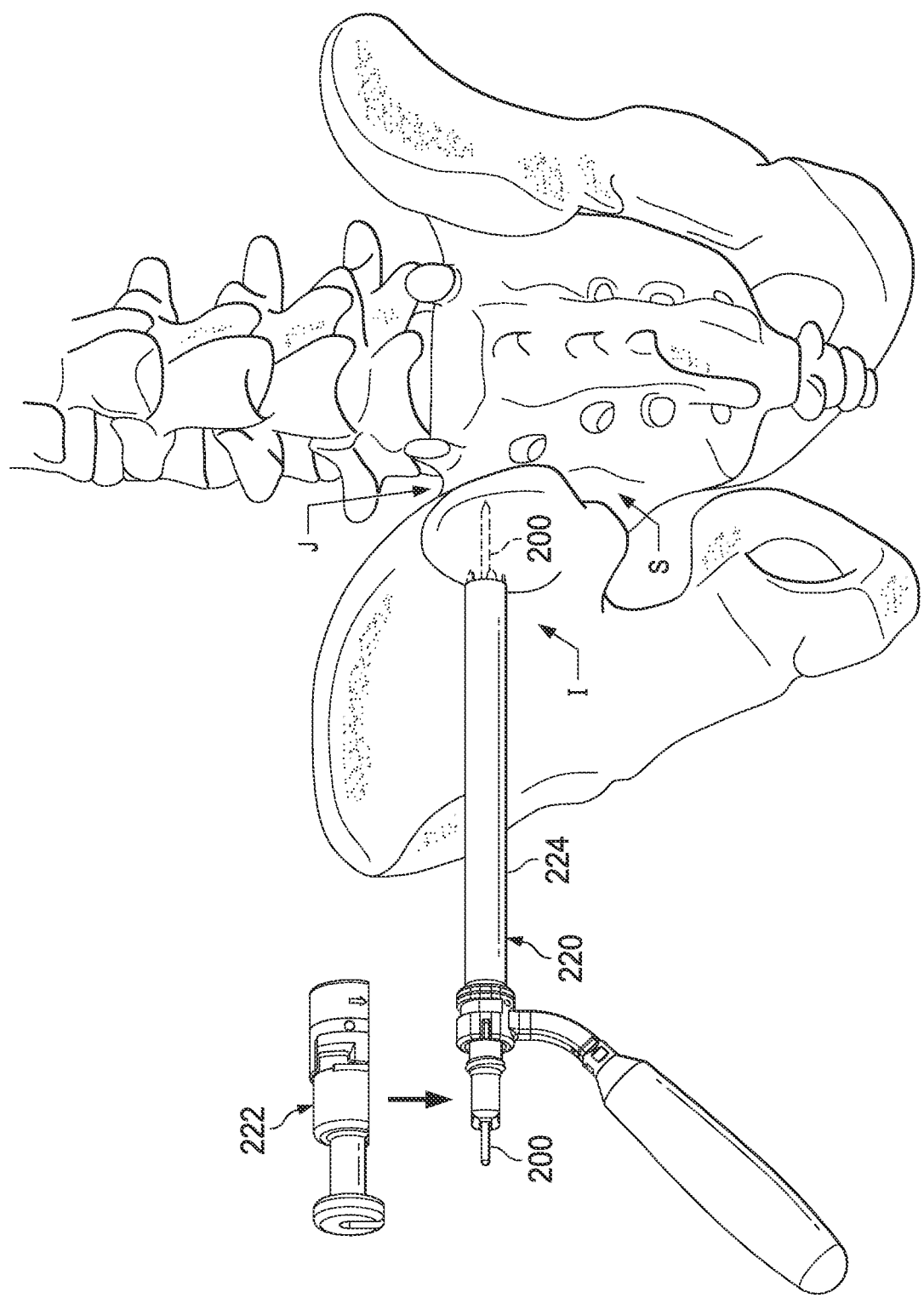
FIG. 8D is a perspective view of a skeletal structure including the sacroiliac joint undergoing a surgical technique according to some example implementations of the present disclosure.
Figure 9:
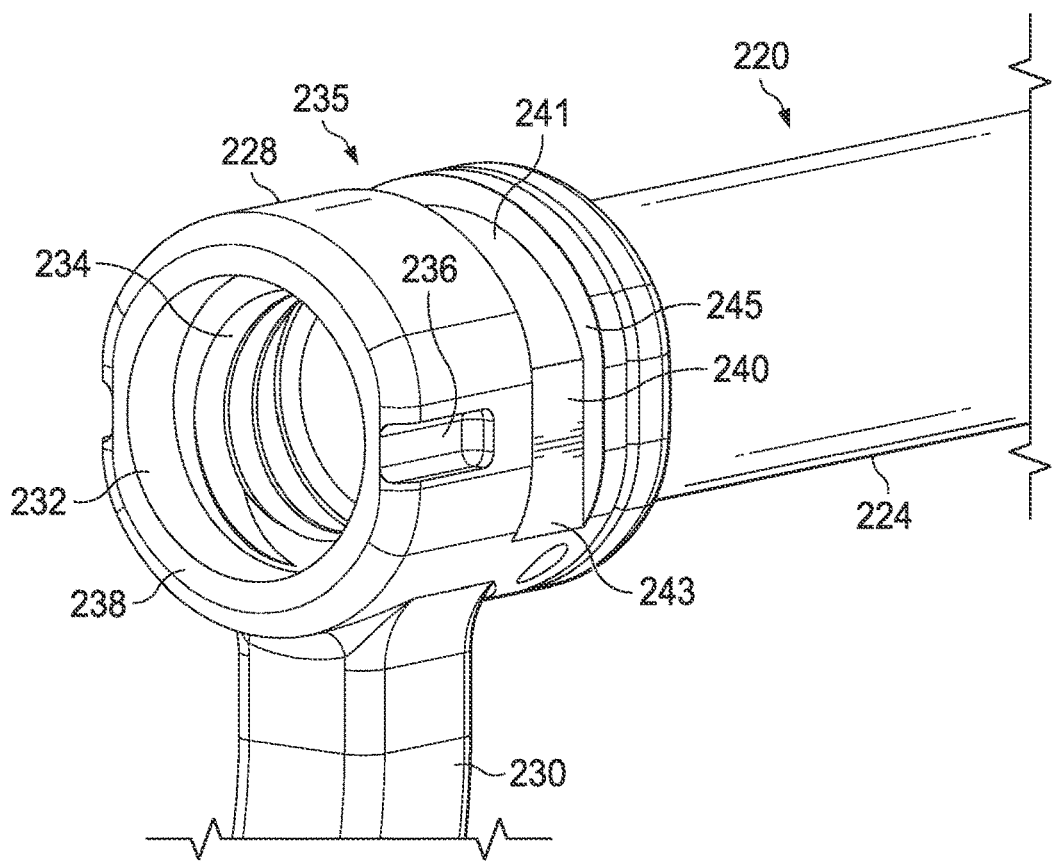
FIG. 9 is a perspective illustration of a surgical instrument according to some example implementations of the present disclosure.
Figure 10:
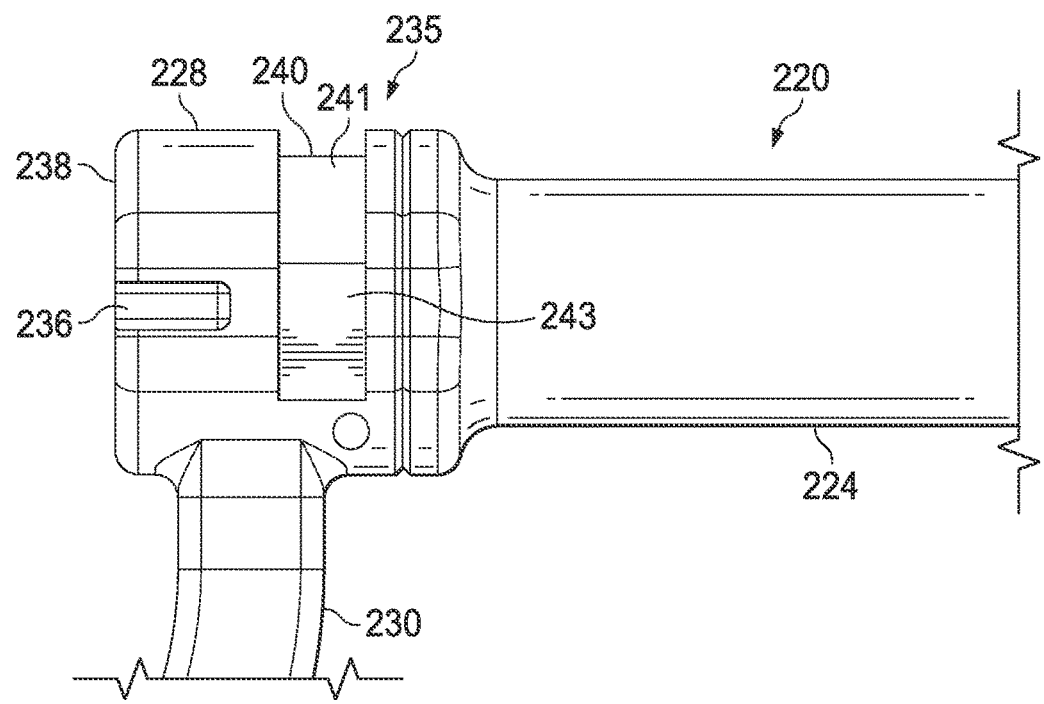
FIG. 10 is a plan view the surgical instrument of FIG. 9 according to some example implementations of the present disclosure.

FIG. 8D shows a striker tube 222 that may be secured to an end of the drill guide 220. FIGS. 9 and 10 show a portion of the drill guide 220 in greater detail, and FIGS. 11 and 12 show the striker tube 222 in greater detail.

Turning first to FIGS. 9 and 10, the drill guide 220 includes a projecting drill guide cannula 224. The distal end 221 (FIG. 8C) of the drill guide cannula 224 may include the spikes 218 or other bone securing features may secure the distal end 226 of the drill guide cannula 224 in place relative to the bone material such as the ilium. The drill guide 220 also includes a proximal end 228 and a handle 230 that extends radially from the proximal end 228. The proximal end 228 includes an opening 232 to the cannula, through which instruments and the implant may be introduced to the patient. In the implementation shown, the opening 232 forms an inner surface of the cannula 224 and includes fastening structure 234 that may enable the drill guide 220 connect with and be secured to other components, such as the pin sleeve 214 discussed above with reference to FIG. 8C. Here, the fastening structure 234 comprises threads, and interface with corresponding fastening structures, such as threads 219 on the pin sleeve 214 in FIG. 8C.

The proximal end 228 of the drill guide 220 may include securing features 235 about its external surface that may enable connection with other instruments and components. In the example shown, the securing features 235 may include cutouts, grooves, threads, or other features. In the implementation shown, the securing features 235 of the drill guide 220 include externally facing cutouts 236 on opposing sides. These cutouts 236 may be open to lateral sides of the drill guide 220 and may open in the rearward direction by intersecting an end face 238 of the drill guide 220 at the proximal end 228. A groove 240, located at the proximal end 228 yet distal of the cutouts 236, may provide additional connection and securement for additional components. In some implementations, the cutouts 236 and the groove 240 are particularly shaped to interface with and secure the striker tube 222 to the drill guide 220. In the implementation shown, the groove 240 is perpendicular to an axis of the cannula 224 and is formed as a neck having regions of increased width on opposing sides. Here, a portion of the groove 240 is formed as an arc 241 concentric with an outer surface of the proximal end 228 of the drill guide 220. A planar portion 243 of the groove 240 intersects the arc 241 and may prevent twisting or rotation of the striker tube 222 when the striker tube is attached to the drill guide 220.

Figure 11:
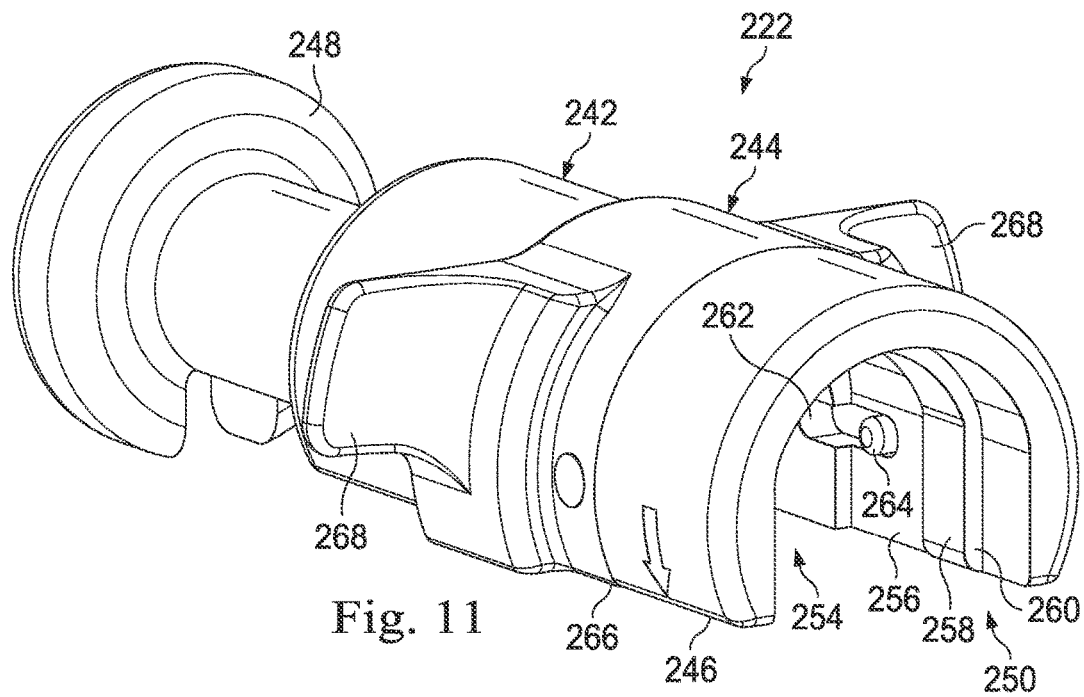
FIG. 11 is a perspective illustration of a surgical instrument according to some example implementations of the present disclosure.
Figure 12:
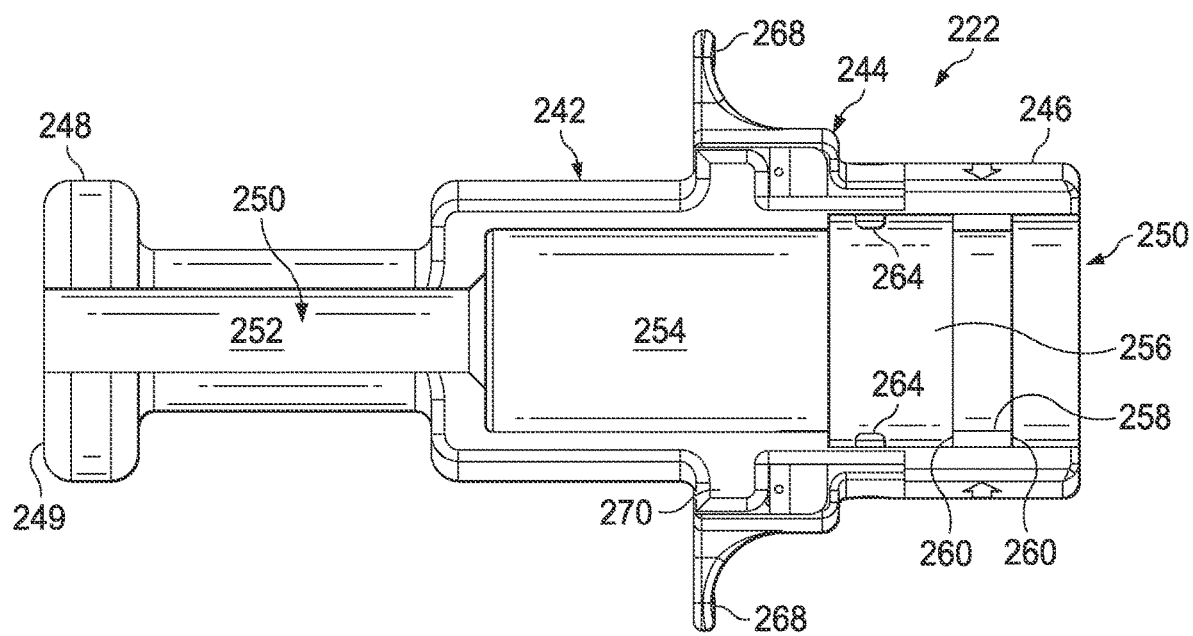
FIG. 12 is a bottom view the surgical instrument of FIG. 11 according to some example implementations of the present disclosure.

The striker tube 222 shown in FIGS. 11 and 12 includes a main body 242 and a sliding collar 244. The main body 242 may be configured to receive an impact from an instrument, such as a mallet, and transfer the force directly to the drill guide 220. This may come into play when a health care provider desires to drive the spikes 218 or other bone securing features at the distal end 221 of the drill guide cannula 224 into bone. Striking the striker tube 222 may protect the drill guide 220 from damage while applying sufficient force for the spikes 218 to penetrate the bone and secure the drill guide 220 in place while the implant technique is carried out.

The main body 242 of the striker tube 222 includes a distal end 246 and a proximal end 248. A longitudinally extending opening 250 extends along one side of the main body 242 from the distal end 246 to the proximal end 248. The proximal end 248 includes a wide impact surface 249 configured to withstand blows of the mallet. A relatively narrow bore 252 and a main central cavity form a part of the opening 250. The narrow bore 252 extends from the proximal end 248 towards the distal end 246 and intersects the central cavity 254 of the main body 242. The main central cavity 254 includes an inner surface 256 shaped to interface with an external surface of the drill guide 220. In this case, the inner surface 256 of the central cavity 254 includes a projecting flange 258 that is shaped to slide into the groove 240 on the drill guide 220. Accordingly, to introduce the flange 258 into the groove 240, the drill guide 220 is laterally displaced relative to the proximal end of the drill guide 220 (as indicated by the arrow in FIG. 8D) so that the flange 258 is received into the groove 240. The flange 258 includes side surfaces 260 that are perpendicular to the longitudinal axis of the striker tube 222, and interface with interfacing side surfaces forming the groove 240. When a health care provider strikes the impact surface 249 of the striker tube 222 at the proximal end 248, the applied load is transferred from the flange 258 on the striker tube to a side surface 245 of the groove 240 at the proximal end 228 of the drill guide 220. The shape of the flange 258 of the striker tube 222 and the groove 240 of the drill guide 220 cooperate to transfer force from the proximal impact surface 249 on the striker tube 222 to the drill guide 220. They also prevent the striker tube 222 from coming off the drill guide 220 in an axial direction, and they prevent the striker tube 222 from rotating on the drill guide 220. As shown in FIG. 11, the inner surface 256 of the central cavity 254 includes axially extending slots 262 that enable a pin 264 attached to the sliding collar 244 to extend into the central cavity 254 and engage the drill guide 220 when the striker tube 222 is associated with the drill guide 220.

The sliding collar 244 fits about an external surface 266 of the main body 242 of the striker tube 222. The sliding collar 244 may displace axially in a proximal or distal direction relative to the main body 242. The sliding collar 244 may lock or unlock the striker tube 222 to the drill guide 220.

In the implementation shown, the sliding collar 244 includes two laterally extending handles 268, and the internally extending pins 264. Further, the sliding collar 244 is shaped to engage a peripheral projecting rim 270 on the main body 242 that holds the sliding collar 244 in place. In use, a health care provider may unlock the striker tube 222 by displacing the sliding collar 244 along the main body 242 so that the pins 264 may depress out of the central cavity 254 and into the side wall of the central cavity 254. The striker tube 222 may then be introduced over the proximal end 228 of the drill guide 220. In so doing, the retracted pins 264 may slide over an external surface of the drill guide 220 until the pins 264 are aligned with the cutouts 236. Likewise, the flange 258 of the main body 242 may slide into or be inserted into the groove 240 of the drill guide 220. Releasing the sliding collar 244 may permit the sliding collar 244 to axially displace in a distal direction and may force the pins 264 into the cutouts 236, thereby preventing lateral removal of the striker tube 222 from the drill guide 220. In some implementations, the sliding collar 244 is biased to a locked condition using springs or other biasing mechanisms.

Figure 8E:
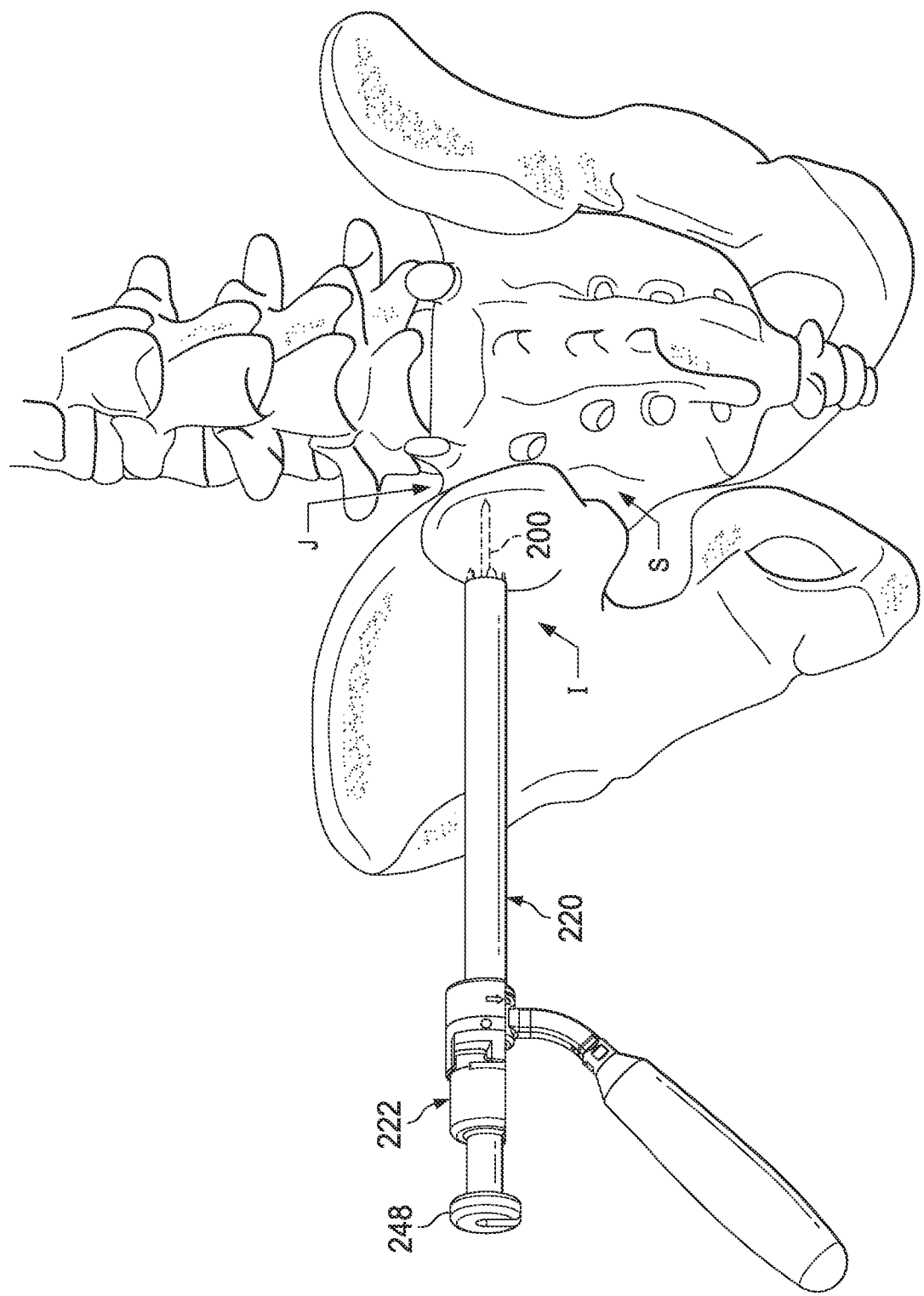
FIG. 8E is a perspective view of a skeletal structure including the sacroiliac joint undergoing a surgical technique according to some example implementations of the present disclosure.

FIG. 8E shows the striker tube 222 attached to the drill guide 220. Applying a load to the proximal end 248 of the striker tube 222 may drive the distal tip of the drill guide 220 into the bone, thereby securing the drill guide 220 in place so long as desired for the surgery.

Figure 8F:
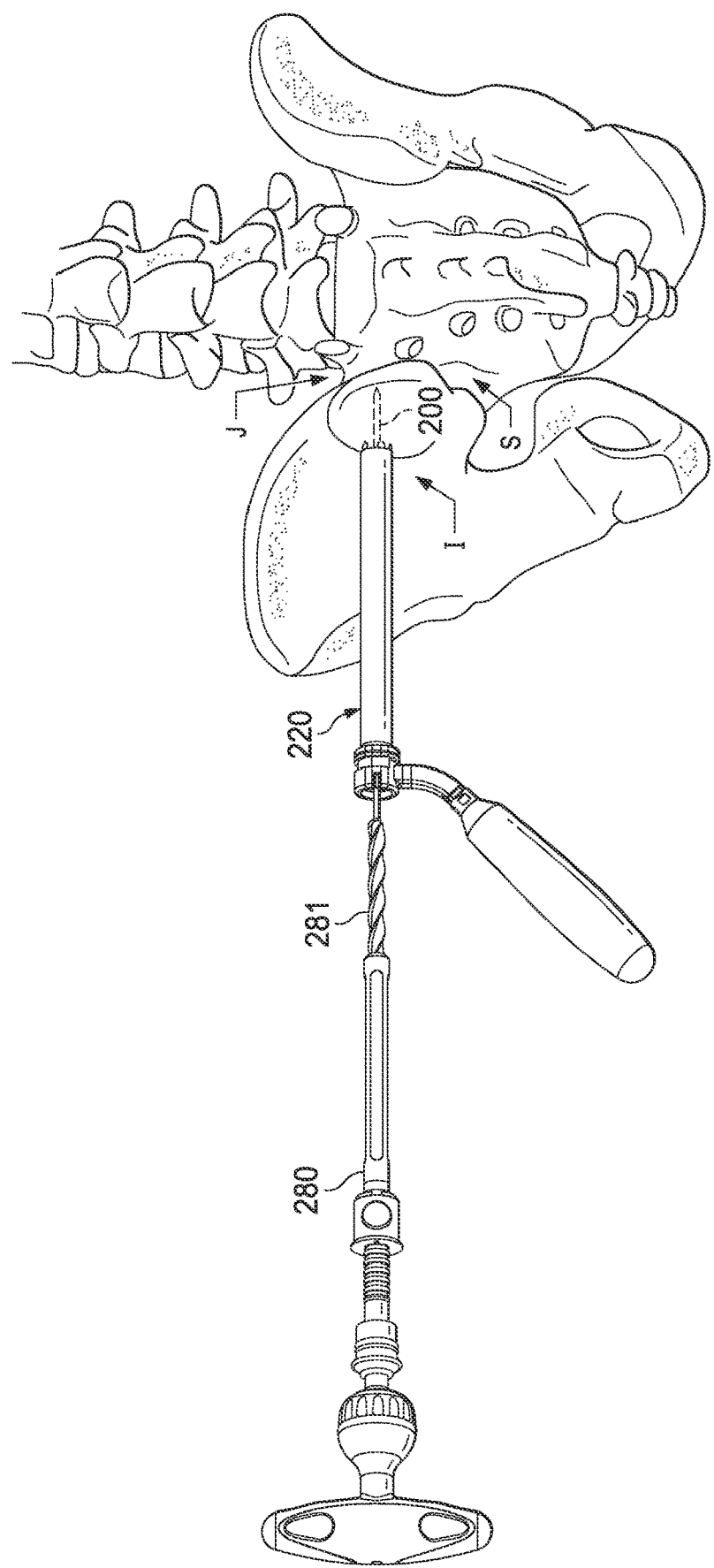
FIG. 8F is a perspective view of a skeletal structure including the sacroiliac joint undergoing a surgical technique according to some example implementations of the present disclosure.

With the drill guide 220 in place, the striker tube 222 may be removed, and as shown in FIG. 8F, a drill 280 with a drill bit 281 may be introduced over the guide pin 200 and through the drill guide 220. The drill 280 may be advanced through the ilium I, across the SI joint J, and into the sacrum S by rotating the drill to create a hole across the joint J. When the hole is drilled, the drill 280 may be removed from the drill guide 220.

Before introducing the implant 100 to drilled hole, the healthcare provider may fill the implant 100 with allograft or autograft. This may be done in either of two different processes. The first process is utilized if the guide pin 200 was previously removed, as may occur when removing the drill 280. In the first process, the healthcare provider may entirely fill the hollow bore 110 of the implant 100 with the allograft or autograft. Once filled, the implant 100 may be loaded onto a screwdriver 282 by inserting the screwdriver into the drive bore 112 of the implant 100, which forms a part of the hollow bore 110. The implant 100, attached to the screwdriver, may then be introduced through the drill guide 220 to the drilled hole.

The alternative second process may be used if the guide pin 200 is still in place in the sacrum S after the drill 280 is removed. In the second process, the healthcare provider may prepare the implant 100 for introduction to the patient by first introducing a second, additional guide pin through the hollow bore 110, and then packing the implant 100 with allograft or autograft about the second additional guide pin to fill the void in the hollow bore 110 between the outer wall of the second additional guide pin and inner wall of the implant 100 that defines the hollow bore 110. The second additional guide pin may then be removed from the hollow bore of the implant 100 while leaving the allograft or autograft in place, thereby forming an open passage through the allograft or autograft in the hollow bore 110. The implant 100 may then be loaded onto the screwdriver 282 by inserting the screwdriver into the drive bore 112.

Figure 8G:
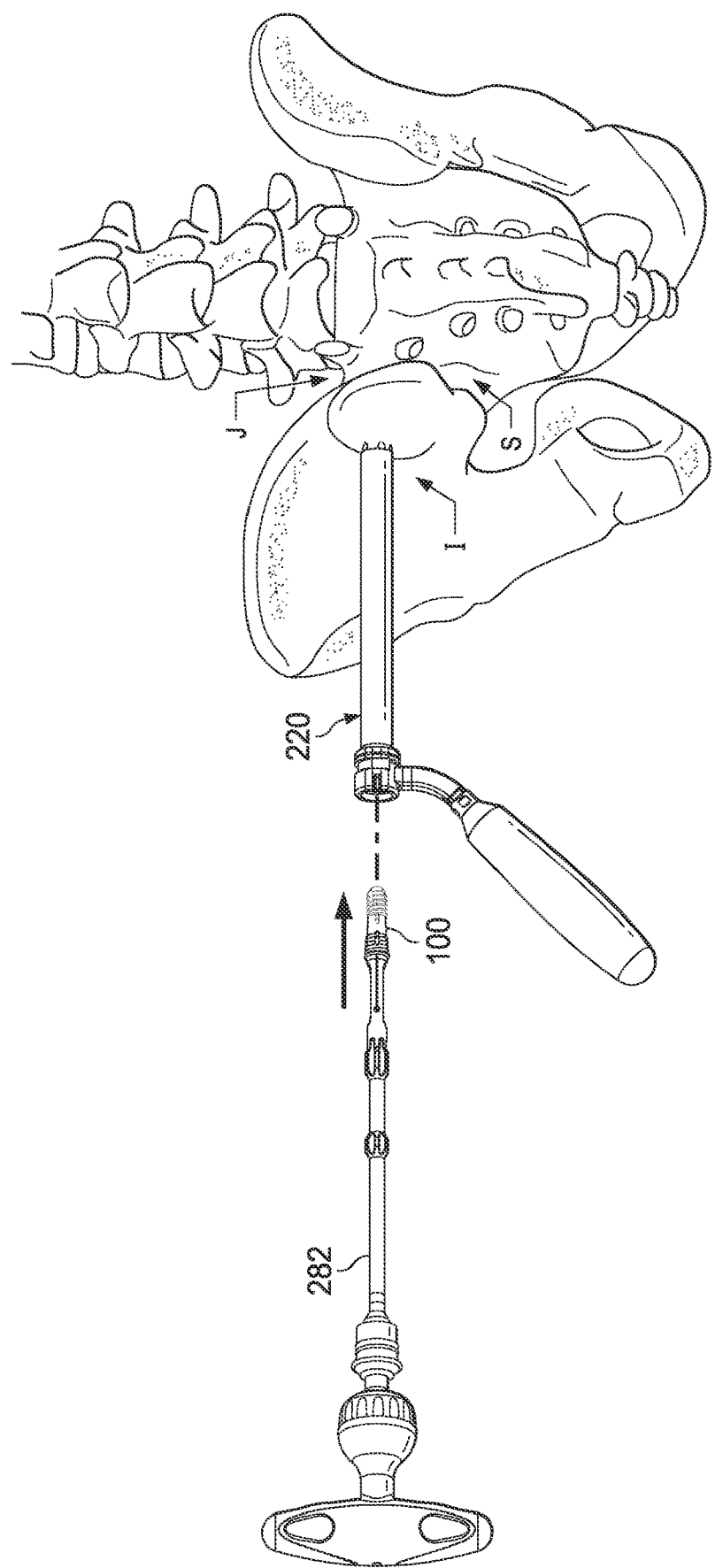
FIG. 8G is a perspective view of a skeletal structure including the sacroiliac joint undergoing a surgical technique according to some example implementations of the present disclosure.

Regardless of whether the health care provider utilized the first or second process for introducing autograft or allograft into the implant 100, the screwdriver 282 and implant 100 are introduced into the drill guide 220 as shown in FIG. 8G. This may include either simply sliding the implant through the drill guide to the drilled pilot hole, or it may include first inserting an end of the guide pin 200 through the bore opening 111 at the distal end 106 of the implant 100 and advancing the implant 100 over the guide pin 200 so that the guide pin 200 passes through the open passage through the allograft or autograft while sliding to the drilled pilot hole.

Figure 8H:
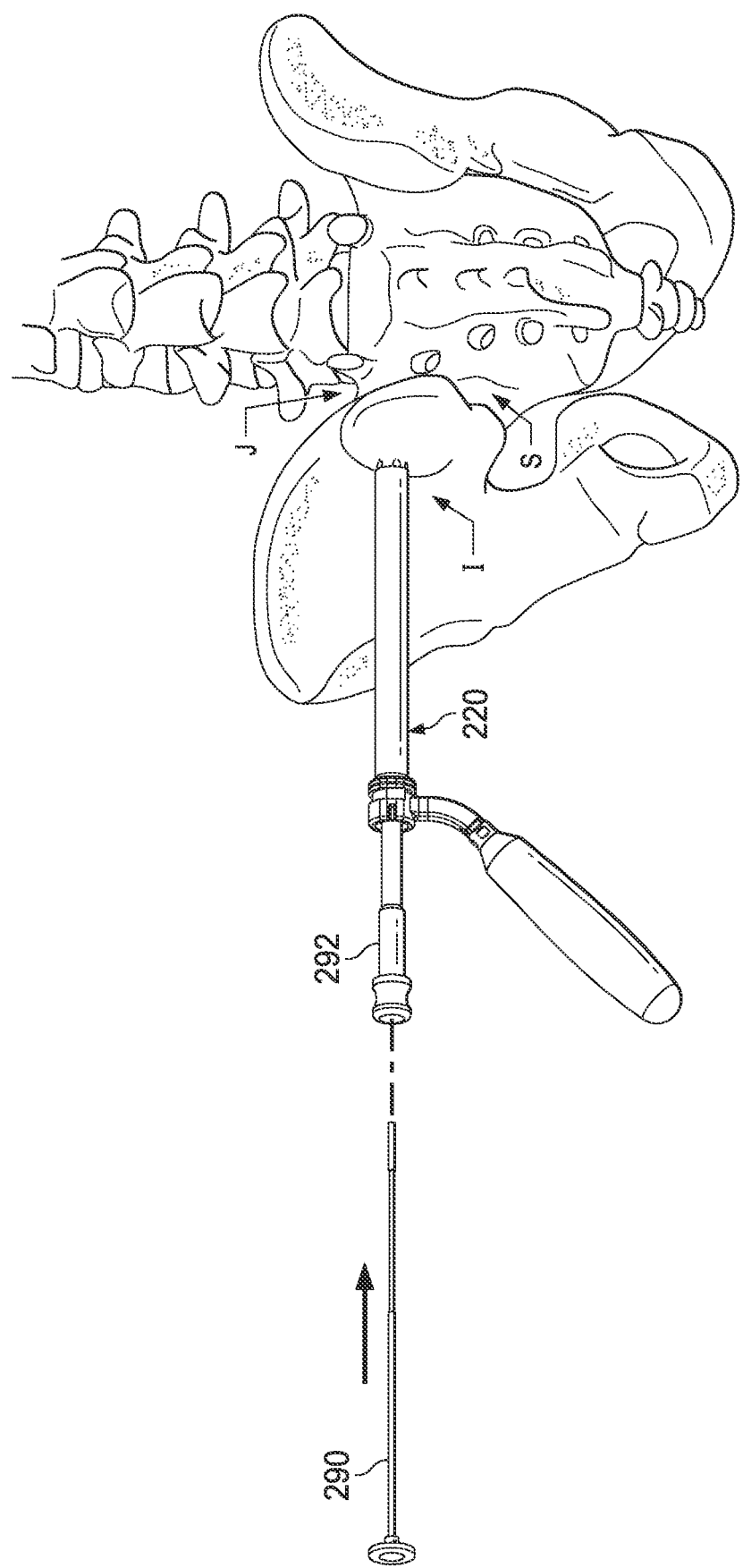
FIG. 8H is a perspective view of a skeletal structure including the sacroiliac joint undergoing a surgical technique according to some example implementations of the present disclosure.

The implant 100 may then be screwed or threaded into the drilled pilot hole and across the joint J. While threading the implant 100 into the bone and across the joint, the distal portion 116 may penetrate the sacrum, and the helical fenestrations 134 may harvest auto graft that will help promote bone growth into the helical fenestrations and fusion of the distal portion 116 of the implant to the bone, such as the sacrum. If the guide pin 200 was still in place while introducing the implant 100, the guide pin may be removed, and additional biologic material may be injected into the open passage through the allograft or autograft in the hollow bore 110, as illustrated in FIG. 8H. FIG. 8H shows a plunger 290 and a packing tube 292, that may form a part of a biologic material injector that may be used to introduce biologic material through the proximal end of the implant 100 to fill the open passageway or any other space that may remain in the previously packed hollow bore 110. The packing tube 292 may be introduced through the drill guide 220 to the implant 100, and the plunger 290 may be introduced through the proximal end of the packing tube 292, thereby forcing the additional biologic material into the implant 100.

During healing, the packed allograft, autograft, and/or other biological material may help promote bone ingrowth into and through the linear slots. The material packed in the hollow bore 110 may be one or more of any suitable biocompatible material that promotes bone growth and healing. In specific implementations, the material may include demineralized bone chips, demineralized bone fibers, and/or allograft. For implementations wherein the substance is biologic, the substance may be autogenic, allogenic, xenogenic, or transgenic. Some implementations include other suitable materials, such as, for example, protein, nucleic acid, carbohydrate, lipids, collagen, allograft bone, autograft bone, cartilage stimulating substances, allograft cartilage, TCP, hydroxyapatite, calcium sulfate, polymer, nanofibrous polymers, growth factors, carriers for growth factors, growth factor extracts of tissues, demineralized bone matrix, dentine, bone marrow aspirate, bone marrow aspirate combined with various osteoinductive or osteoconductive carriers, concentrates of lipid derived or marrow derived adult stem cells, umbilical cord derived stem cells, adult or embryonic stem cells combined with various osteoinductive or osteoconductive carriers, transfected cell lines, bone forming cells derived from periosteum, combinations of bone stimulating and cartilage stimulating materials, committed or partially committed cells from the osteogenic or chondrogenic lineage, or combinations of any of the above. Introduced materials may be homogenous, or generally a single substance, or may be heterogeneous, or a mixture of substances.

In some implementations, the porous sleeve 104 may be treated prior to or during implantation to promote bone ingrowth and fusion of the joint. The porous sleeve 104 may be treated with or may include form therein any of the materials described herein, or other materials that may help promote bone growth or fusion.

In some instances, the implant 100 is disposed with the proximal portion threadably secured in the ilium I and the distal portion threadably secured in the sacrum S, and the porous sleeve 104 extending transversely through the intersection of the SI joint.

With the implant 100 disposed across the SI joint J, the joint may be immobile. Additionally, the porous sleeve 104 may be disposed across the joint to permit and promote bonding and ingrowth of bone at the joint-facing surface of the ilium I and the sacrum S. Thus, the porous sleeve 104 may promote faster healing and stronger bonding with the surrounding tissue by promoting bone growth about the entire 360° radius of the distal portion 116. In addition, the helical fenestrations 134 and the linear slots 150 promote additional ingrowth reaching toward the hollow bore 110. With the implant 100 in place, the drill tube 220 may be removed, from the patient, and the incisions may be closed.

While certain example embodiments of the present disclosure have been described and shown in the accompanying drawings, it is to be understood that such embodiments are merely illustrative of and not restrictive to the broad disclosed concepts, and that the embodiments of the present disclosure not be limited to the specific constructions and arrangements shown and described, since various other modifications may occur to those ordinarily skilled in the art.

What is claimed is:

1. An implant, comprising:
a distal portion comprising a distal thread and a first fenestration in the distal thread, the distal thread comprising a first thread minor and a first thread major;
a middle portion adjacent the distal portion, the middle portion being devoid of threads and comprising a porous outer surface, the porous outer surface comprising a leading end and a trailing end, the leading end comprising a diameter larger than the first thread minor of the distal portion; and
a proximal portion adjacent the middle portion, the proximal portion comprising a proximal thread, the proximal thread comprising a second thread minor and a second thread major, wherein the second thread minor is equal to or larger than the trailing end of the middle portion for at least a portion of the proximal thread.

2. The implant of claim 1, wherein the second thread minor is tapered differently than the second thread major.

3. The implant of claim 1, comprising a plurality of linear slots disposed radially about the middle portion.

4. The implant of claim 1, wherein the distal thread comprises a first pitch and the proximal thread comprises a second pitch, the second pitch of the proximal thread being different than the first pitch of the distal thread.

5. The implant of claim 1, wherein the porous outer surface of the middle portion is substantially cylindrical from a leading end to a trailing end.

6. The implant of claim 1, wherein the distal portion and the proximal portion are formed of a nonporous material.

7. The implant of claim 1, wherein the middle portion comprises a porous structure formed by a 3D printed lattice structure.

8. The implant of claim 7, wherein the porous structure has a porosity in a range of about 45% to 85%.

9. The implant of claim 1, wherein the implant includes a proximal end, and the proximal portion is tapered outwardly toward the proximal end.

10. The implant of claim 9, wherein the proximal portion comprises a screw head disposed at the proximal end of the implant, the screw head having an outer periphery with the diameter greater than a diameter of the second thread major.

11. A surgical instrument set comprising:
a drill tube having a distal end and a proximal end, the distal end having one or more anchoring devices disposed thereon;
a striker tube comprising a main body and a sliding collar, the striker tube comprising an opening in a lateral wall of the main body such that the striker tube is laterally insertable over the proximal end of the drill tube in a direction transverse to a longitudinal axis of the drill tube, the sliding collar being displaceable to lock and unlock the striker tube from the drill tube; and
wherein the drill tube comprises an exterior surface with a cutout formed therein, the cutout being sized to receive a displaceable portion of the striker tube.

12. The surgical instrument set of claim 11, wherein the exterior surface of the drill tube comprises one of a flange and a recess, wherein an interior surface of the striker tube comprises the other of the flange and the recess, the flange and the recess sized to mate to transfer loading on the striker tube through the flange and recess to the drill tube.

13. The surgical instrument set of claim 11, wherein when the sliding collar is configured to lock the striker tube to the drill tube, movement of the striker tube is at least partially restricted in the direction transverse to the longitudinal axis of the drill tube and a direction substantially opposite the direction transverse to the longitudinal axis of the drill tube.

14. The surgical instrument set of claim 11, wherein the displaceable portion is a biasing member.

15. A surgical instrument set comprising:
a drill tube having a distal end and a proximal end, the distal end having one or more anchoring devices disposed thereon; and
a striker tube comprising a main body and a sliding collar, the striker tube comprising an opening in a lateral wall of the main body such that the striker tube is laterally insertable over the proximal end of the drill tube in a direction transverse to a longitudinal axis of the drill tube, the sliding collar comprising a member, the member being displaceable relative to the striker tube to lock and unlock the striker tube from the drill tube.

16. The surgical instrument set of claim 15, wherein the drill tube comprises an exterior surface with a cutout formed therein, the cutout being sized to receive the member.

17. The surgical instrument set of claim 15, wherein an exterior surface of the drill tube comprises one of a flange and a recess, wherein an interior surface of the striker tube comprises the other of the flange and the recess, the flange and the recess sized to mate to transfer loading on the striker tube through the flange and recess to the drill tube.

18. The surgical instrument set of claim 15, wherein when the sliding collar is configured to lock the striker tube to the drill tube, movement of the striker tube is at least partially restricted in the direction transverse to the longitudinal axis of the drill tube and a direction substantially opposite the direction transverse to the longitudinal axis of the drill tube.

19. The surgical instrument set of claim 15, wherein the member is a biasing member.

20. The surgical instrument set of claim 15, wherein the member is operatively coupled to a spring.

* * * * *